United States Patent
Pohl et al.

(10) Patent No.: US 9,381,247 B2
(45) Date of Patent: *Jul. 5, 2016

(54) MAGNESIUM COMPOSITIONS FOR MODULATING THE PHARMACOKINETICS AND PHARMACODYNAMICS OF INSULIN AND INSULIN ANALOGS, AND INJECTION SITE PAIN

(71) Applicant: Biodel Inc., Danbury, CT (US)

(72) Inventors: Roderike Pohl, Sherman, CT (US); Robert Hauser, Columbia, MD (US); Ming Li, Yorktown Heights, NY (US); Bryan R. Wilson, Brewster, NY (US)

(73) Assignee: Biodel Inc., Danbury, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/826,806

(22) Filed: Mar. 14, 2013

(65) Prior Publication Data

US 2014/0113856 A1   Apr. 24, 2014

Related U.S. Application Data

(60) Provisional application No. 61/704,066, filed on Sep. 21, 2012, provisional application No. 61/624,844, filed on Apr. 16, 2012.

(51) Int. Cl.
| | | |
|---|---|---|
| *A61K 47/02* | (2006.01) | |
| *A61K 38/28* | (2006.01) | |
| *A61K 9/00* | (2006.01) | |
| *A61K 47/12* | (2006.01) | |
| *A61K 47/18* | (2006.01) | |

(52) U.S. Cl.
CPC .............. *A61K 47/02* (2013.01); *A61K 9/0019* (2013.01); *A61K 38/28* (2013.01); *A61K 47/12* (2013.01); *A61K 47/183* (2013.01)

(58) Field of Classification Search
None
See application file for complete search history.

(56) References Cited

U.S. PATENT DOCUMENTS

| | | | |
|---|---|---|---|
| 4,196,196 A | | 4/1980 | Tiholiz |
| 5,070,186 A | * | 12/1991 | Joergensen ................ 530/304 |
| 7,279,457 B2 | | 10/2007 | Pohl |
| 2007/0235365 A1 | | 10/2007 | Pohl |
| 2008/0085298 A1 | | 4/2008 | Pohl |
| 2008/0090753 A1 | | 4/2008 | Pohl |
| 2008/0096800 A1 | | 4/2008 | Pohl |
| 2009/0280532 A1 | | 11/2009 | Gorfien |
| 2009/0304665 A1 | * | 12/2009 | Frost et al. ................ 424/94.5 |
| 2010/0151435 A1 | | 6/2010 | Thatte |

FOREIGN PATENT DOCUMENTS

| | | |
|---|---|---|
| EP | 1044016 | 3/2005 |
| WO | 2009134380 | 11/2009 |
| WO | 2012006283 | 1/2012 |

OTHER PUBLICATIONS

Shoaybi et al. (The effect of Magnesium sulfate on reducing Propofol injection pain in elective surgeries; Tehran University Medical Journal; vol. 64(2), May 2007: 30-34).*

Pohl et al, "Ultra-rapid absorption of recombinant human insulin induced by zinc chelation and surface charge masking", J. Diabetes Sci.Technol, 6(4)755-763) (2012).

Shin, et al., "Evaluation of dose effects of magnesium sulfate on rocuronium injection pain and hemodynamic changes by laryngoscopy and endotracheal intubation", Korean J Anesthesiol, 60(5):329-33 (2011).

Steiner, et al., "A novel insulin formulation with a more rapid onset of action", Diabetologia, 51:1602-1606 (2008).

* cited by examiner

*Primary Examiner* — James H. Alstrum-Acevedo
*Assistant Examiner* — Tara Martinez
(74) *Attorney, Agent, or Firm* — Pabst Patent Group LLP

(57) ABSTRACT

Compositions and methods for modulating injection site pain associated with rapid acting injectable insulin formulations have been developed for subcutaneous injection. The formulations contain insulin in combination with a zinc chelator such as ethylenediaminetetraacetic acid ("EDTA"), a dissolution/stabilization agent such as citric acid, a magnesium salt, and, optionally, additional excipients. New presentations include rapid acting concentrated insulin formulations and a way to enhance the absorption of commercially available rapid acting analog formulations by mixing them with a vial containing dry powder excipients that accelerate their absorption. Devices for mixing excipient and insulin together at the time of administration, while minimizing residence time of the mixture, are also described.

25 Claims, 6 Drawing Sheets

Insulin Charge Distribution

- Cationic residues on insulin are clustered
- Multivalent anions may neutralize (mask) the charge ns, loss of kidney function, nerve damage and loss of sensation and poor circulation in the periphery, potentially requiring amputation of the extremities.

MAGNESIUM COMPOSITIONS FOR MODULATING THE PHARMACOKINETICS AND PHARMACODYNAMICS OF INSULIN AND INSULIN ANALOGS, AND INJECTION SITE PAIN

CROSS REFERENCE TO RELATED APPLICATIONS

This application claims benefit of U.S. Provisional Application No. 61/704,066, filed Sep. 21, 2012, and 61/624,844, filed Apr. 16, 2012, both of which are herein incorporated by reference in their entirety.

FIELD OF THE INVENTION

The invention is in the general field of injectable rapid acting drug delivery insulin formulations and methods of their use and reduction of pain on injection.

BACKGROUND OF THE INVENTION

Diabetes Overview

Glucose is a simple sugar used by all the cells of the body to produce energy and support life. Humans need a minimum level of glucose in their blood at all times to stay alive. The primary manner in which the body produces blood glucose is through the digestion of food. When a person does not get glucose from food digestion, glucose is produced from stores in the tissue and released by the liver. The body's glucose levels are regulated by insulin. Insulin is a peptide hormone that is naturally secreted by the pancreas. Insulin helps glucose enter the body's cells to provide a vital source of energy.

When a healthy individual begins a meal, the pancreas releases a natural spike of insulin called the first-phase insulin release. In addition to providing sufficient insulin to process the glucose coming into the blood from digestion of the meal, the first-phase insulin release acts as a signal to the liver to stop making glucose while digestion of the meal is taking place. Because the liver is not producing glucose and there is sufficient additional insulin to process the glucose from digestion, the blood glucose levels of healthy individuals remain relatively constant and their blood glucose levels do not become too high.

Diabetes is a disease characterized by abnormally high levels of blood glucose and inadequate levels of insulin. There are two major types of diabetes—Type 1 and Type 2. In Type 1 diabetes, the body produces no insulin. In the early stages of Type 2 diabetes, although the pancreas does produce insulin, either the body does not produce the insulin at the right time or the body's cells ignore the insulin, a condition known as insulin resistance.

Even before any other symptoms are present, one of the first effects of Type 2 diabetes is the loss of the meal-induced first-phase insulin release. In the absence of the first-phase insulin release, the liver will not receive its signal to stop making glucose. As a result, the liver will continue to produce glucose at a time when the body begins to produce new glucose through the digestion of the meal. As a result, the blood glucose level of patients with diabetes goes too high after eating, a condition known as hyperglycemia. Hyperglycemia causes glucose to attach unnaturally to certain proteins in the blood, interfering with the proteins' ability to perform their normal function of maintaining the integrity of the small blood vessels. With hyperglycemia occurring after each meal, the tiny blood vessels eventually break down and leak. The long-term adverse effects of hyperglycemia include blindness, loss of kidney function, nerve damage and loss of sensation and poor circulation in the periphery, potentially requiring amputation of the extremities.

Between two and three hours after a meal, an untreated diabetic's blood glucose becomes so elevated that the pancreas receives a signal to secrete an inordinately large amount of insulin. In a patient with early Type 2 diabetes, the pancreas can still respond and secretes this large amount of insulin. However, this occurs at the time when digestion is almost over and blood glucose levels should begin to fall. This inordinately large amount of insulin has two detrimental effects. First, it puts an undue extreme demand on an already compromised pancreas, which may lead to its more rapid deterioration and eventually render the pancreas unable to produce insulin. Second, too much insulin after digestion leads to weight gain, which may further exacerbate the disease condition.

Current Treatments for Diabetes and their Limitations

Because patients with Type 1 diabetes produce no insulin, the primary treatment for Type 1 diabetes is daily intensive insulin therapy. The treatment of Type 2 diabetes typically starts with management of diet and exercise. Although helpful in the short-run, treatment through diet and exercise alone is not an effective long-term solution for the vast majority of patients with Type 2 diabetes. When diet and exercise are no longer sufficient, treatment commences with various non-insulin oral medications. These oral medications act by increasing the amount of insulin produced by the pancreas, by increasing the sensitivity of insulin-sensitive cells, by reducing the glucose output of the liver or by some combination of these mechanisms. These treatments are limited in their ability to manage the disease effectively and generally have significant side effects, such as weight gain and hypertension. Because of the limitations of non-insulin treatments, many patients with Type 2 diabetes deteriorate over time and eventually require insulin therapy to support their metabolism. As their insulin resistance progresses, higher and higher doses of insulin are required to lower glucose levels. Concentrated insulin up to U-500 (500 units per ml) is commercially available for these patients, but it is limited to basal use due to a slow absorption profile.

Insulin therapy has been used for more than 80 years to treat diabetes. This therapy usually involves administering several injections of insulin each day. These injections consist of administering a long-acting basal injection one or two times per day and an injection of a fast-acting insulin at meal-time. Although this treatment regimen is accepted as effective, it has limitations. First, patients generally dislike injecting themselves with insulin due to the inconvenience and pain of needles. As a result, patients tend not to comply adequately with the prescribed treatment regimens and are often improperly medicated.

More importantly, even when properly administered, insulin injections do not replicate the natural time-action profile of insulin. In particular, the natural spike of the first-phase insulin release in a person without diabetes results in blood insulin levels rising within several minutes of the entry into the blood of glucose from a meal. By contrast, injected insulin enters the blood slowly, with peak insulin levels occurring within 80 to 100 minutes following the injection of regular human insulin.

A potential solution is the injection of insulin directly into the vein of diabetic patients immediately before eating a meal. In studies of intravenous injections of insulin, patients exhibited better control of their blood glucose for 3 to 6 hours following the meal. However, for a variety of medical reasons, intravenous injection of insulin before each meal is not a practical therapy.

One of the key improvements in insulin treatments was the introduction in the 1990s of rapid-acting insulin analogs, such as HUMALOG® (insulin lispro), NOVOLOG® (insulin aspart) and APIDRA® (insulin glulisine). However, even with the rapid-acting insulin analogs, peak insulin levels typically occur within 50 to 70 minutes following the injection. Because the rapid-acting insulin analogs do not adequately mimic the first-phase insulin release, diabetics using insulin therapy continue to have inadequate levels of insulin present at the initiation of a meal and too much insulin present between meals. This lag in insulin delivery can result in hyperglycemia early after meal onset. Furthermore, the excessive insulin between meals may result in an abnormally low level of blood glucose known as hypoglycemia. Hypoglycemia can result in loss of mental acuity, confusion, increased heart rate, hunger, sweating and faintness. At very low glucose levels, hypoglycemia can result in loss of consciousness, coma and even death. According to the American Diabetes Association, or ADA, insulin-using diabetic patients have on average 1.2 serious hypoglycemic events per year, many of which events require hospital emergency room visits by the patients.

The rapidity of insulin action is dependent on how quickly it is absorbed. When regular human insulin is injected subcutaneously at 100 IU/ml, the formulation is primarily composed of hexamers (approximately 36 kDa) which are not readily absorbed due to their size and charge. Located within the hexamer are two zinc atoms that stabilize the molecule. Post injection, a concentration driven dynamic equilibrium occurs in the subcutaneous tissue causing the hexamers to dissociate into dimers (about 12 kDa), then monomers (about 6 kDa). Historically, these regular human insulin formulations require approximately 120 min. to reach maximum plasma concentration levels.

Insulin formulations with a rapid onset of action, such as VIAject®, are described in U.S. Pat. No. 7,279,457, and U.S. Published Applications 2007/0235365, 2008/0085298, 2008/90753, and 2008/0096800, and Steiner, et al., *Diabetologia*, 51:1602-1606 (2008). The rapid acting insulin formulations were designed to create insulin formulations that provide an even more rapid pharmacokinetic profile than insulin analogs, thereby avoiding the patient becoming hyperglycemic in the first hour after injection and hypoglycemic two to four hours later. The rapid onset of VIAJECT® results from the inclusion of two key excipients, a zinc chelator such as disodium EDTA (EDTA) and/or calcium disodium EDTA which rapidly dissociates insulin hexamers into monomers and dimers and a dissolution/stabilization agent such as citric acid which stabilizes the dissociated monomers and dimers prior to being absorbed into the blood (Pohl et al, *J. Diabetes Sci. and Technology,* 2012. 6(4)755-763).

Unfortunately, early clinical trials with this product showed injection site discomfort. Inclusion of calcium, either as calcium chloride and/or the calcium salt of the EDTA, decreased injection site pain, supporting the theory that pain arose due to removal of calcium from the extracellular fluid in the injection site vicinity. However, the addition of calcium altered the pharmacokinetics. The concentrated insulin formulations were developed with the same concept in mind, however, these formulations have a unique profile combining ultrarapid action with some extended duration of action. They are particularly well suited for insulin resistant individuals who require prandial insulin and basal insulin injections. With this U-400 formulation, the need for two injections is eliminated, since the absorption profile could fulfill both prandial and intermediate acting insulin (i.e. NPH) needs. In addition, these concentrated insulin formulations could be used with insulin pumps for insulin resistant patients. The reduced volume could lead to future design of miniature pumps, or bihormonal pumps such as those being developed for the artificial pancreas.

It is an object of this invention to provide compositions of ultra-rapid acting injectable insulin compositions with reduced injection site discomfort. It is also an object of the present invention to provide specific concentrated insulin formulations for treating insulin resistant diabetic which modulate the pharmacokinetics and pharmacodynamics of injectable insulin compositions by increasing the rate of absorption from the site of subcutaneous injection.

SUMMARY OF THE INVENTION

Compositions and methods for modulating the pharmacokinetics and pharmacodynamics of U-100, ultra rapid analogs and U-400 ultra-rapid acting injectable insulin formulations with improved injection site tolerability, have been developed. The formulations contain insulin in combination with a zinc chelator such as ethylenediamine tetraacetic acid ("EDTA"), a dissolution/stabilization agent such as citric acid and/or sodium citrate, one or more magnesium compounds, and, optionally, additional excipients.

In one embodiment, the formulation contains recombinant human insulin, sodium EDTA, a dissolution/stabilization agent such as citric acid and/or sodium citrate, and one or more magnesium compounds, such as magnesium EDTA, $Mg(OH)_2$, $MgSO_4$, or combinations thereof. In a particular embodiment, the magnesium compound is $MgSO_4$. The concentration of magnesium compounds is from about 0.1 to about 10 mg/ml, preferably from about 0.1 to about 5 mg/ml, more preferably from about 0.1 to about 2 mg/ml, most preferably from about 0.2 to about 2 mg/ml. In some embodiments, the formulations contain about 0.2-0.3 mg/ml $Mg(OH)_2$ (e.g., 0.282), about 1.7-2.0 magnesium EDTA (e.g., 1.89), and/or about 0.4-0.5 magnesium sulfate (e.g., 0.481). Stability is enhanced by optimizing m-cresol and citrate ion concentration. The concentration of the insulin in the formulation varies from 100-500 units/mL.

In the preferred embodiment, the formulations are administered via subcutaneous injection.

BRIEF DESCRIPTION OF THE DRAWINGS

FIG. 3, 0-480 minutes) post-dose of the Mg EDTA insulin formulations BIOD 123 and 125 compared to HUMALOG®.

DETAILED DESCRIPTION OF THE INVENTION

Figure 1:
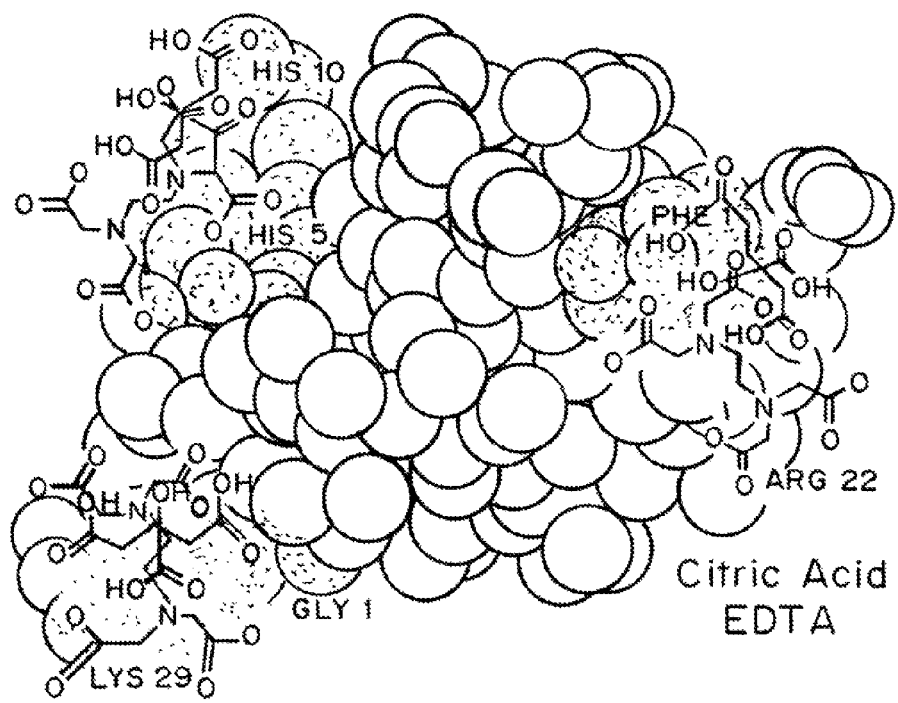
FIG. 1 is a three dimensional schematic of insulin showing exposed surface charges and overlaid with molecules ("dissolution and chelating agents") of appropriate size to mask the charge.

The insulin formulations disclosed herein are administered immediately prior to a meal or at the end of a meal. The formulations are designed to be absorbed into the blood faster than the currently marketed rapid-acting insulin or insulin analogs. One of the key features of the formulation of insulin is that a zinc chelator is included which disassociates, or separates, the hexameric form of insulin to the monomeric and/or dimeric form of insulin and prevents or minimizes re-association to the hexameric form post injection, thereby promoting rapid absorption into the bloodstream post injection. It has been discovered that a systematic relationship exists between the concentration of zinc chelator, such as disodium EDTA, and the speed of glucose absorption from the blood. Variation in EDTA concentration alters the pharmacokinetics and pharmacodynamics of rapid acting insulin formulations.

While not being bound by theory, a possible explanation for the injection site discomfort of the EDTA-citric acid-insulin formulation is chelation of extracellular calcium by disodium EDTA. Calcium is in the extracellular fluid at a concentration of approximately 1 mM, and is essential for excitation-contraction coupling, muscle function, neurotransmitter release, and cellular metabolism. Loss of local calcium can cause muscle tetany, which is a disorder marked by intermittent tonic muscular contractions, accompanied by fibrillary tremors, paresthesias and muscular pain. To avoid this interaction, a formulation removing calcium from the extracellular fluid should not be used.

The substitution of disodium EDTA with the calcium chelated form of EDTA (i.e., calcium disodium EDTA) can reduce injection site pain as compared to the same amount of disodium EDTA. However, calcium disodium EDTA slightly delays the rate of absorption in vivo. Therefore, magnesium was used instead of calcium to chelate the excess EDTA. The addition of magnesium to the formulation increased injection site tolerability and did not alter the rate of insulin absorption.

In one embodiment, the formulation contains recombinant human insulin, sodium EDTA, a dissolution/stabilization agent such as citric acid and/or sodium citrate, and one or more magnesium compounds, such as magnesium EDTA, $Mg(OH)_2$, $MgSO_4$, or combinations thereof. In a particular embodiment, the magnesium compound is $MgSO_4$. The concentration of magnesium compounds is from about 0.1 to about 10 mg/ml, preferably from about 0.1 to about 5 mg/ml, more preferably from about 0.1 to about 2 mg/ml, most preferably from about 0.2 to about 2 mg/ml. In some embodiments, the formulations contain about 0.2-0.3 mg/ml $Mg(OH)_2$ (e.g., 0.282), about 1.7-2.0 magnesium EDTA (e.g., 1.89), and/or about 0.4-0.5 magnesium sulfate (e.g., 0.481). Stability is enhanced by optimizing m-cresol and citrate ion concentration. The concentration of the insulin in the formulation varies from 100-500 units/mL.

I. Definitions

As used herein, "insulin" refers to human or non-human, recombinant, purified or synthetic insulin or insulin analogues, unless otherwise specified.

As used herein, "Human insulin" is the human peptide hormone secreted by the pancreas, whether isolated from a natural source or made by genetically altered microorganisms. As used herein, "non-human insulin" is the same as human insulin but from an animal source such as pig or cow.

As used herein, an insulin analogue is an altered insulin, different from the insulin secreted by the pancreas, but still available to the body for performing the same action as natural insulin. Through genetic engineering of the underlying DNA, the amino acid sequence of insulin can be changed to alter its ADME (absorption, distribution, metabolism, and excretion) characteristics. Examples include insulin lispro, insulin glargine, insulin aspart, insulin glulisine, and insulin detemir. The insulin can also be modified chemically, for example, by acetylation. As used herein, human insulin analogues are altered human insulin which is able to perform the same action as human insulin.

As used herein, a "chelator" or "chelating agent", refers to a chemical compound that has the ability to form one or more bonds to zinc ions. The bonds are typically ionic or coordination bonds. The chelator can be an inorganic or an organic compound. A chelate complex is a complex in which the metal ion is bound to two or more atoms of the chelating agent.

As used herein, a "solubilizing agent", is a compound that increases the solubility of materials in a solvent, for example, insulin in an aqueous solution. Examples of solubilizing agents include surfactants such as polysorbates (TWEEN®); solvents such as ethanol; micelle forming compounds, such as oxyethylene monostearate; and pH-modifying agents.

As used herein, a "dissolution/stabilization agent" or "dissolution/stabilizing agent" is an acid or a salt thereof that, when added to insulin and EDTA, enhances the transport and absorption of insulin relative to HCl and EDTA at the same pH, as measured using the epithelial cell transwell plate assay described in the examples below. HCl is not a dissolution/stabilization agent but may aid in solubilization. Citric acid is a dissolution/stabilization agent when measured in this assay.

As used herein, "inorganic magnesium compound" or "inorganic magnesium salt" refers to compounds in which the anion does not contain one or more carbon atoms.

As used herein, "organic magnesium compound" or "organic magnesium salt" refers to compounds in which the anion contains one or more carbon atoms.

As used herein, an "excipient" is an inactive substance other than a chelator or dissolution/stabilization agent, used as a carrier for the insulin or used to aid the process by which a product is manufactured. In such cases, the active substance is dissolved or mixed with an excipient.

As used herein, a "physiological pH" is between 6.8 and 7.6, preferably between 7 and 7.5, most preferably about 7.4.

As used herein, "Cmax" is the maximum or peak concentration of a drug observed after its administration.

As used herein, "Tmax" is the time at which maximum concentration (Cmax) occurs. As used herein, ½ Tmax is the time at which half maximal concentration (½ Cmax) of insulin occurs in the blood. This may also be expressed as T50% earlymax.

II. Formulations

Formulations include insulin or an insulin analog, a zinc chelator and a dissolution/stabilizing agent(s), magnesium, and, optionally, one or more other excipients. In the preferred embodiment, the formulations are suitable for subcutaneous administration and are rapidly absorbed into the subcutaneous tissue. The choice of dissolution/stabilization agent and chelator, the concentration of both the dissolution/stabilization agent and the chelator, and the pH that the formulation is adjusted to, all have a profound effect on the efficacy of the system. While many combinations have efficacy, the preferred embodiment is chosen for reasons including safety, comfort, stability, regulatory profile, and performance.

In the preferred embodiment, at least one of the formulation ingredients is selected to mask charges on the insulin. This is believed to facilitate the transmembrane transport of the insulin and thereby increase both the onset of action and bioavailability for the insulin. The ingredients are also selected to form compositions that dissolve rapidly in aqueous medium. Preferably the insulin is absorbed and transported to the plasma quickly, resulting in a rapid onset of action, preferably beginning within about 5 minutes following administration and peaking at about 15-30 minutes following administration.

The chelator, such as EDTA, chelates the zinc within the insulin, thereby removing the zinc from the insulin molecule. This causes the hexameric insulin to dissociate into its dimeric and monomeric forms and retards reassembly into the hexamer state post injection. Since these two forms exist in a concentration-driven equilibrium, as the monomers are absorbed, more monomers are created. Thus, as insulin monomers are absorbed through the subcutaneous tissue, additional dimers dissemble to form more monomers. The monomeric form has a molecular weight that is less than one-sixth the molecular weight of the hexameric form, thereby markedly increasing both the speed and quantity of insulin absorption. To the extent that the chelator (such as EDTA) and/or dissolution/stabilization agent (such as citric acid) hydrogen bond with the insulin, it is believed that they mask the charge on the insulin, facilitating its transmembrane transport and thereby increasing both the onset of action and bioavailability of the insulin.

A magnesium salt has been found to not significantly alter the pharmacokinetic profile while at the same time decreasing the injection site pain.

In the preferred embodiment, M-cresol is added for its anti-microbial properties and enhancement of shelf life.

Insulin

Insulin or insulin analogs may be used in this formulation. Preferably, the insulin is recombinant human insulin. Recombinant human insulin is available from a number of sources. The dosages of the insulin depend on its bioavailability and the patient to be treated. Insulin is generally included in a dosage range of 1.5-200 IU, depending on the level of insulin resistance of the individual. Typically, insulin is provided in 100 IU vials, though other presentations of 200, 400 or 500 U/ml are described herein. In the most preferred embodiment the injectable formulation is a volume of 1 ml containing 100 U of insulin. Additional embodiments include higher concentration insulin formulations, the most preferred being U-400.

There are several differing types of commercial insulin available for diabetes patients. These types of insulins vary according to (1) how long they take to reach the bloodstream and start reducing blood glucose levels; (2) how long the insulin operates at maximum strength; and (3) how long the insulin continues to have an effect on blood sugar.

Fast Acting Insulin

Fast acting insulins are intended to respond to the glucose derived from ingestion of carbohydrates during a meal. Fast acting insulins start to work within one to 20 minutes, peaking about one hour later and lasting from three to five hours. Fast acting insulin takes about two hours to fully absorb into the systemic circulation. Fast acting insulins include regular recombinant human insulin (such as HUMULIN®, marketed by Eli Lilly, and NOVALIN®, marketed by Novo Nordisk A/S) which are administered in an isotonic solution at pH 7. Bovine and porcine insulins, which differ in several amino acids to human insulin, but are bioactive in humans, are also fast acting insulins.

Concentrated Insulin Formulations

More concentrated forms of insulin are provided for insulin resistant individuals. The commercially available formulation Humulin R U-500 has a very long duration of action and is suitable for basal use only due to its slow release profiles.

Rapid Acting Insulin.

Some diabetes patients use rapid-acting insulin at mealtimes, and long-acting insulin for 'background' continuous insulin. This group includes insulins that have been modified or have altered locations of amino acids in order to enhance their rate of absorption.

At present there are three types of rapid-acting commercial insulin analogs available: insulin lispro (Lysine-Proline insulin, sold by Eli Lilly as HUMALOG®), insulin glulisine (sold by Sanofi-Aventis as APIDRA®) and insulin aspart (sold by Novo Nordisk as NOVOLOG®).

Intermediate Acting Insulin

Intermediate-acting insulin has a longer lifespan than short-acting insulin but it is slower to start working and takes longer to reach its maximum strength. Intermediate-acting insulin usually starts working within 2-4 hours after injection, peaks somewhere between 4-14 hours and remains effective up to 24 hours. Types of intermediate-acting insulin include NPH (Neutral Protamine Hagedorn) and LENTE insulin. NPH insulin contains protamine which slows down the speed of absorption so that the insulin takes longer to reach the bloodstream but has a longer peak and lifespan. Intermediate acting insulins may be combined with rapid acting insulins at neutral pH, to reduce the total number of injections per day.

Blends of immediate acting insulin and intermediate acting insulin: Blends of rapid acting insulin and NPH insulin are commercially available to fulfill the need for prandial and basal use in a single injection. These insulin blends may be regular recombinant insulin based (HUMULIN® 70/30 (70% human insulin isophane and 30% human insulin, Eli Lilly) or analog based, such HUMALOG® Mix75/25 (75% insulin lispro protamine suspension and 25% insulin lispro solution) (Eli Lilly) and are 100 U-ml. These blends use a protamine insulin suspension (HUMULIN® or HUMALOG® based) to extend the duration of action insulin action with HUMULIN®R (regular human insulin) or HUMALOG®R to cover the prandial needs.

Long Acting Insulin

Examples of long acting insulins are insulin glargine (marketed under the tradename LANTUS®, Sanofi Aventis) and insulin detemir (LEVEMIR®, Novo Nordisk A/S). The extended duration of action of LANTUS® is normally induced by the pH elevation from 4 to 7 post subcutaneous injection. This changes the solubility of the insulin glargine, creating a microprecipitate. This microprecipate slowly dissolves in the subcutaneous tissue, sustaining its glucose lowering effect for up to 24 hours. It differs from human insulin by having a glycine instead of asparagine at position 21 and two arginines added to the carboxy-terminus of the beta-chain.

Dissolution/Stabilization Agents

Certain polyacids appear to mask charges on the insulin, enhancing uptake and transport, as shown in FIG. 1. Those acids which are effective as dissolution/stabilization agents include acetic acid, ascorbic acid, citric acid, glutamic acid, aspartic acid, succinic acid, fumaric acid, maleic acid, adipic acid, and salts thereof, relative to hydrochloric acid, which is not a charge masking agent. The effective acids are all diacids or polyacids. For example, if the active agent is insulin, a preferred dissolution/stabilization agent is citric acid and/or sodium citrate. Hydrochloric acid may be used for pH adjustment, in combination with any of the formulations, but is not a dissolution/stabilization agent.

The acid may be added directly or in the form of a salt, which dissociates in aqueous solution. Salts of the acids include sodium acetate, ascorbate, citrate, glutamate, aspartate, succinate, fumarate, maleate, and adipate. Salts of organic acids can be prepared using a variety of bases including, but not limited to, metal hydroxides, metal oxides, metal carbonates and bicarbonates, metal amines, as well as ammonium bases, such as ammonium chloride, ammonium carbonate, etc. Suitable metals include monovalent and polyvalent metal ions. Exemplary metals ions include the Group I metals, such as lithium, sodium, and potassium; Group II metals, such as barium, magnesium, calcium, and strontium; and metalloids such as aluminum. Polyvalent metal ions may be desirable for organic acids containing more than carboxylic acid group since these ions can simultaneously complex to more than one carboxylic acid group.

The range of dissolution/stabilization agent corresponds to an effective amount of citric acid in combination with insulin and disodium EDTA. For example, a range of $9.37 \times 10^{-4}$ M to $9.37 \times 10^{-2}$ M citric acid corresponds with a weight/volume of about 0.18 mg/ml to about 18 mg/ml if the citric acid is anhydrous citric acid with a molar mass of approximately 192 gram/mole. In some embodiments the amount of anhydrous citric acid ranges from about 50% of 1.8 mg/ml (0.9 mg/ml) to about 500% of 1.8 mg/ml (9 mg/ml), more preferably from about 75% of 1.8 mg/ml (1.35 mg/ml) to about 300% of 1.8 mg/ml (5.4 mg/ml). In a preferred embodiment, the amount of anhydrous citric acid can be about 1.8 mg/ml, or about 2.7 mg/ml, or about 3.6 mg/ml, or about 5.4 mg/ml. In the most preferred embodiment, the amount of citric acid is 2.7 mg/ml of the injectable formulation. The weight/volume may be adjusted, if for example, citric acid monohydrate or trisodium citrate or another citric acid is used instead of anhydrous citric acid.

The preferred dissolution/stabilization agent when the insulin formulation has a pH in the physiological pH range is sodium citrate.

In a particularly preferred embodiment, the formulation contains a mixture of disodium EDTA and citric acid. In general the ratio of citric acid to disodium EDTA is in the range of 300:100, for example, 100:120, 100:100, 200:100, 150:100, 300:200, and 500:100.

Chelators

In the preferred embodiment, a zinc chelator is mixed with the insulin. The chelator may be ionic or non-ionic. Chelators include ethylenediaminetetraacetic acid (EDTA), EGTA, alginic acid, alpha lipoic acid, dimercaptosuccinic acid (DMSA), CDTA (1,2-diaminocyclohexanetetraacetic acid), and trisodium citrate (TSC). Hydrochloric acid is used in conjunction with TSC to adjust the pH, and in the process gives rise to the formation of citric acid, which is a dissolution/stabilization agent.

The chelator captures the zinc from the insulin, thereby favoring the monomeric or dimeric form of the insulin over the hexameric form and facilitating absorption of the insulin into the tissues surrounding the site of administration (e.g. mucosa, or fatty tissue). In addition, the chelator hydrogen may bond to the insulin, thereby aiding the charge masking of the insulin monomers and facilitating transmembrane transport of the insulin monomers.

In the preferred embodiment, the chelator is EDTA. In the most preferred embodiment, the formulation contains insulin, disodium EDTA, calcium chloride, and a dissolution/stabilization agent such as citric acid or sodium citrate.

A range of $2.42 \times 10^{-4}$ M to $9.68 \times 10^{-2}$ M EDTA corresponds to a weight/volume of about 0.07 mg/ml to about 28 mg/ml if the EDTA is Ethylenediaminetetraacetic acid with a molar mass of approximately 292 grams/mole. Reduction of the concentration of EDTA can slow the rate of insulin absorption and delay the glucose response to the insulin injection. Further increases in this concentration provide negligible gains in absorption rate.

In preferred embodiments, the amount of EDTA ranges from about 5% of 1.8 mg/ml (0.09 mg/ml) to about 500% of 1.8 mg/ml (9 mg/ml), more preferably about 15% of 1.8 mg/ml (0.27 mg/ml) to about 200% of 1.8 mg/ml (3.6 mg/ml). For example, the amount of EDTA can be 0.1 mg/ml, 0.25 mg/ml, 1.0 mg/ml, 1.8 mg/ml, 2.0 mg/ml, or 2.4 mg/ml of EDTA.

Reduction of the concentration of EDTA can slow the rate of insulin absorption and delay the glucose response to the insulin injection. In a preferred embodiment, the chelator is disodium EDTA, preferably, in an amount equal to or less than 2.0 mg/ml. Further increases in this concentration provide negligible gains in absorption rate. In some embodiments, the EDTA is a combination of disodium EDTA and calcium disodium EDTA. For example, in one embodiment, the EDTA is about 0.27-0.3 mg/ml of disodium EDTA in combination with about 1.8-2.0 mg/ml of calcium disodium EDTA. In some embodiments, the EDTA is between about 1.8-2.0 mg/ml of calcium disodium EDTA or disodium EDTA and $CaCl_2$.

Magnesium Compounds

The formulations contain one or more pharmaceutically acceptable magnesium compounds. As discussed above, EDTA can cause irritation at the injection site due to the complexation of endogenous calcium at the site of administration. While the inclusion of calcium EDTA can ameliorate this irritation, the addition of calcium EDTA to the formulation slows down the insulin absorption. In order to minimize or prevent injection site irritation and not change the rate of subcutaneous absorption, one or more magnesium compounds are incorporated into the formulation.

The magnesium compounds can be an inorganic and/or organic magnesium salt. Suitable magnesium inorganic salts include, but are not limited to, magnesium hydroxide ($Mg(OH)_2$), magnesium sulfate $Mg(SO_4)$, magnesium halides, such as magnesium chloride ($MgCl_2$), magnesium bromide ($MgBr_2$), and magnesium iodide ($MgI_2$); magnesium pyrophosphate, magnesium sulfate heptahydrate, and magnesium oxide ($MgO_2$).

Suitable magnesium organic salts include, but are not limited to, magnesium EDTA, magnesium lactate, amino acid chelates, such as magnesium aspartate; magnesium acetate, magnesium carbonate ($Mg(CO_3)_2$), magnesium citrate, and magnesium gluconate.

In particular embodiments, the one or more magnesium compounds is magnesium EDTA, $Mg(OH)_2$, $MgSO_4$, or combinations thereof. In one embodiment, the one or more magnesium compounds is $MgSO_4$.

The concentration of the one or more magnesium compounds is from about 0.1 to about 10 mg/ml, preferably from about 0.1 to about 5 mg/ml, more preferably from about 0.1 to about 2 mg/ml, most preferably from about 0.2 to about 2 mg/ml. In some embodiments, the formulations contains about 0.2-0.3 mg/ml Mg(OH)$_2$ (e.g., 0.282), about 1.7-2.0 magnesium EDTA (e.g., 1.89), and/or about 0.4-0.5 magnesium sulfate (e.g., 0.481).

Excipients

Pharmaceutical compositions may be formulated in a conventional manner using one or more physiologically acceptable carriers comprising excipients and auxiliaries which facilitate processing of the active compounds into preparations which can be used pharmaceutically. Formulation of drugs is discussed in, for example, Hoover, John E., Remington's Pharmaceutical Sciences, Mack Publishing Co., Easton, Pa. (1975), and Liberman, H. A. and Lachman, L., Eds., Pharmaceutical Dosage Forms, Marcel Decker, New York, N.Y. (1980).

In the preferred embodiment, one or more solubilizing agents are included with the insulin to promote rapid dissolution in aqueous media. Suitable solubilizing agents include wetting agents such as polysorbates, glycerin and poloxamers, non-ionic and ionic surfactants, food acids and bases (e.g. sodium bicarbonate), and alcohols, and buffer salts for pH control. In a preferred embodiment the pH is adjusted using hydrochloric acid (HCl) or sodium hydroxide (NaOH). The pH of the injectable formulation is typically between about 6.8-7.8, preferably about 7.1

Stabilizers are used to inhibit or retard drug decomposition reactions which include, by way of example, oxidative reactions. A number of stabilizers may be used. Suitable stabilizers include buffers; such as citrates, phosphates and acetates; polysaccharides, such as cellulose and cellulose derivatives, sulfated polysaccharides complex and simple alcohols, such as glycerol (or glycerin, or glycerine); bacteriostatic agents such as phenol, benzyl alcohol, meta-cresol (m-cresol), 2-phenoxyethanol and methyl/propyl paraben; isotonic agents, such as sodium chloride, glycerol (or glycerin, or glycerine), cyclic amino acids, amino acids and glucose; lecithins, such as example natural lecithins (e.g. egg yolk lecithin or soya bean lecithin) and synthetic or semisynthetic lecithins (e.g. dimyristoylphosphatidylcholine, dipalmitoylphosphatidylcholine or distearoyl-phosphatidylcholine; phosphatidic acids; phosphatidylethanolamines; phosphatidylserines such as distearoyl-phosphatidylserine, dipalmitoylphosphatidylserine and diarachidoylphospahtidylserine; phosphatidylglycerols; phosphatidylinositols; cardiolipins; sphingomyelins. Also, solvent or co-solvent systems (ethanol, PEG-300, glycerin, propylene glycol) and solubilizing agents such as polysorbates 20/80; poloxamer 188 and sorbitol. In one example, the stabilizer may be a combination of glycerol, bacteriostatic agents and isotonic agents. The most preferred formulations include glycerin and m-cresol. The range for glycerin is about 1-35 mg/ml, preferably about 10-25 mg/ml, most preferably about 19.5-22.5 mg/ml. The range for m-cresol is about 0.75-6 mg/ml, preferably about 1.8-3.2 mg/ml, most preferably about 2 or 3 mg/ml. Calcium chloride can be added to the formulation to "neutralize" any free EDTA and sodium citrate and/or citric acid is added to stabilize the dissociated monomer. Calcium chloride is more typically added to the formulation when the chelator is disodium EDTA. It is added in matched approximately equimolar concentration to the disodium EDTA. For example, if the disodium EDTA is 5 mM, then 5 mM calcium chloride should be used. The effective range is 80-120% of disodium EDTA. A further possible candidate for this is magnesium, added in similar quantities. The range for calcium chloride is about 0.1-10 mM, preferably more preferably about 2.5-7.5 mM, most preferably about 5 mM.

In some embodiments, commercial preparations of insulin and insulin analogs preparations can be used as the insulin of the formulations disclosed herein. Therefore, the final formulation can include additional excipients commonly found in the commercial preparations of insulin and insulin analogs, including, but not limited to, zinc, zinc chloride, phenol, sodium phosphate, zinc oxide, disodium hydrogen phosphate, sodium chloride, tromethamine, and polysorbate 20. These may also be removed from these commercially available preparations prior to adding the chelator and dissociating/stabilizing agents described herein.

Examples of formulations are described in detail in the Examples below. Calcium-EDTA-citric acid formulations contain: 100 U/ml of insulin, 1.8 mg/ml of calcium disodium EDTA, 2.7 mg/ml of citric acid, 20.08 mg/ml of glycerin, and 3.0 mg/ml of m-cresol ("BIOD-105 or 100 U/ml of insulin or an insulin analog, 1.8 mg/ml of disodium EDTA, 2.7 mg/ml of citric acid, 18.1 mg/ml of glycerin, 2.0 mg/ml of m-cresol, and 5 mM of calcium chloride ("BIOD-107").

Insulin formulations containing one or more magnesium compounds were prepared as described in Table 1.

TABLE 1

Magnesium-EDTA-Insulin Formulation Compositions

| Form | Insulin | IU/ml | Na2EDTA mg/ml | Mg(OH2)2 mg/ml | MgEDTA mg/ml | Citric Acid mg/ml | NaCitrate | Glycerin mg/ml | M-Cresol mg/ml | phenol | Disodium phosphate | ZnO | A3 mg/ml | MgSO4 mg/ml |
|---|---|---|---|---|---|---|---|---|---|---|---|---|---|---|
| Linjeta | RHI | 100 | 1.8 | | | 1.8 | | 22 | 3 | — | — | | | |
| BIOD-120 | RHI | 100 | 1.8 | | | 1.8 | | 22 | 3 | | | | | 0.481 (4 mM) |
| BIOD-121 | RHI | 100 | 1.8 | | | 1.8 | | 18 | 3 | | | | 0.3 | 0.481 (4 mM) |
| BIOD-123 | RHI | 100 | 1.5 | | | 1.5 | | 22 | 3 | | | | | 0.481 (4 mM) |
| BIOD-126 | RHI | 100 | | | 1.89 | 1.8 | | 22 | 3 | | | | | |
| BIOD-127/128 | RHI | 100 | 1.8 | 0.282 | | 1.8 | | 22 | 3 | | | | | |
| BIOD-250 | IL | 100 | 0.45 | | | | 2.4 | 16 | 3.15 | .01 | 1.88 | .0197 | | .481 |
| BIOD-531 | RHI | 400 | 3.6 | | | 1.8 | | 16 | 2 | | | | | .481 |

IL = Insulin Lispro; RHI = Recombinant human insulin

III. Methods of Making the Formulations

In a preferred embodiment, the injectable formulation contains insulin, disodium and/or calcium disodium EDTA, citric acid, saline or glycerin, m-Cresol and chloride magnesium salt. In the most preferred embodiment, the subcutaneous injectable formulation is produced by combining water, disodium EDTA, magnesium salt such as $MgSO_4$, citric acid, glycerin, m-Cresol and insulin by sterile filtration into multiuse injection vials or cartridges.

Methods of making the injectable insulin formulations are described in detail in the Examples below.

In one embodiment, the EDTA is added to the formulation(s) prior to the citric acid. In another embodiment, sodium citrate is added instead of citric acid. In the preferred embodiment, citric acid is added to the formulation(s) prior to the EDTA. In one preferred embodiment, the components of the formulation are added to water: citric acid, EDTA, glycerin, m-Cresol, magnesium salt and insulin. Glycerol and m-Cresol are added as a solution while citric acid, EDTA and magnesium salt may be added as powder, crystalline or pre-dissolved in water In some embodiments, the subcutaneous injectable formulation is produced by mixing water, citric acid, EDTA, glycerin and m-Cresol to form a solution (referred to as the "diluent") which is filtered and sterilized. The insulin is separately added to water, sterile filtered and a designated amount is added to a number of separate sterile injection bottles which is then lyophilized to form a powder. The lyophilized powder is stored separately from the diluent to retain its stability. Prior to administration, the diluent is added to the insulin injection bottle to dissolve the insulin and create the final reconstituted product.

In another embodiment, the insulin is in solution and the excipients are lyophilized, spray dried and are added to the insulin prior to injection. In yet another embodiment, the excipients are made as a concentrated liquid and introduced to the liquid insulin prior to injection.

After the predetermined amount of insulin is subcutaneously injected into the patient, the remaining insulin solution may be stored, preferably with refrigeration. In a preferred embodiment, the insulin is prepared as an aqueous solution at about pH 7.0, in vials or cartridges and kept at 4° C.

IV. Methods of Using Formulations

The formulations may be injected subcutaneously or intramuscularly. The formulation is designed to be rapidly absorbed and transported to the plasma for systemic delivery.

Formulations containing insulin as the active agent may be administered to type 1 or type 2 diabetic patients before or during a meal. Due to the rapid absorption, the compositions can shut off the conversion of glycogen to glucose in the liver, thereby preventing hyperglycemia, the main cause of complications from diabetes and the first symptom of type 2 diabetes. Currently available, standard, subcutaneous injections of human insulin must be administered about one half to one hour prior to eating to provide a less than desired effect, because the insulin is absorbed too slowly to shut off the production of glucose in the liver. These new ultrarapid acting formulations may be taken closer to the meal. A potential benefit to this formulation with enhanced pharmacokinetics may be a decrease in the incidence or severity of obesity that is a frequent complication of insulin treatment.

Example 1

Effect of Calcium disodium EDTA Concentration on Injection Site Discomfort in Humans Materials and Methods Each milliliter of VIAJECT® 7 (VJ 7) contains: 3.7 mg (100 IU) of recombinant human insulin, 1.8 mg of citric acid, 1.8 mg of disodium EDTA, 22.07 mg of glycerin, 3.0 mg of m-Cresol as a preservative, and sodium hydroxide and/or hydrochloric acid to adjust the pH to approximately 7.

Each milliliter of BIOD 102 contains: 3.7 mg (100 IU) of recombinant human insulin, 1.8 mg of citric acid, 2.4 mg of calcium disodium EDTA, 15.0 mg of glycerin, 3.0 mg of m-cresol as a preservative, and sodium hydroxide and/or hydrochloric acid to adjust the pH to approximately 7.1.

Each milliliter of BIOD 103 contains: 3.7 mg (100 IU) of recombinant human insulin, 1.8 mg of citric acid, 0.25 mg of disodium EDTA, 2.0 mg of calcium disodium EDTA, 15.0 mg of glycerin, 3.0 mg of m-cresol as a preservative, and sodium hydroxide and/or hydrochloric acid to adjust the pH to approximately 7.1.

Each solution was injected subcutaneously into a human volunteer and the volunteer was asked to rate the pain associated with the injection.

Basic pharmacokinetic parameters Cmax, Tmax, and ½ Tmax were estimated without non-linear modeling A t-test was performed on the data from each formulation compared to VJ7.

Results

As shown in Table 2, the samples containing calcium disodium EDTA (BIOD 102 and BIOD 103) had slightly lower Cmax and later Tmax than the samples containing only disodium EDTA (VJ 7).

TABLE 2

Comparison of calcium disodium EDTA with disodium EDTA Pharmacokinetic Data

| Variable | BIOD 102 | BIOD 103 | VIAJECT® 7 (VJ7) | BIOD 102 vs VJ7 Ratio/Difference (CI) | BIOD 103 vs VJ7 Ratio/Difference (CI) |
|---|---|---|---|---|---|
| $AUC_{0-480}$ | 10005.6 | 10139.6 | 9844.8 | 1.02 (0.98, 1.06) | 1.03 (0.99, 1.07) |
| Cmax | 54.0 | 53.4 | 66.1 | 0.82 (0.68, 0.98) | 0.81 (0.68, 0.96) |
| $T_{50\%}$ (Early) | 12.9 | 17.3 | 11.0 | 1.9 (−3.0, 6.8) | 6.4 (1.8, 11.0) |
| Tmax | 73.1 | 63.9 | 34.2 | 38.9 (17.0, 60.8) | 29.7 (9.0, 50.1) |
| $T_{50\%}$ (Late) | 210.6 | 206.4 | 116.4 | 94.2 (49.6, 138.8) | 90.0 (48.2, 131.7) |

VIAJECT® 7: 1.8 mg of disodium EDTA
BIOD 102: 2.4 mg of calcium disodium EDTA
BIOD 103: 0.25 mg of disodium EDTA, 2.0 mg of calcium disodium EDTA These results demonstrate that the calcium formulations have a significantly slower rate of uptake than the original insulin, sodium EDTA, citric acid formulation, as indicated by the mean times to half maximal insulin concentrations and the time to maximal insulin concentrations (Table 2).

Injection of the insulin formulations containing calcium disodium EDTA resulted in significantly less injection site pain than the disodium EDTA samples, as shown by Table 3.

TABLE 3

Injection Site Discomfort Data

| Variable | BIOD 102 | BIOD 103 | VIAJECT ® 7 (VJ7) | BIOD 102 vs VJ7 p-value | BIOD 103 vs VJ7 p-value |
|---|---|---|---|---|---|
| VAS | 7.7 | 12.4 | 21.0 | 0.026 | 0.109 |
| Severity | 0.55 | 0.56 | 1.10 | 0.030 | 0.025 |
| Relative | 2.84 | 2.98 | 3.58 | 0.023 | 0.244 |

VAS: 0 = None; 100 = Worst possible;
VR Absolute Discomfort: 0 = None, 1 = Mild, 2 = Moderate, 3 = Severe
VR Relative (to usual injections): 1 = Much less; 2 = Less; 3 = Equal; 4 = Increased; 5 = Much increased Example 2

Study of the Rate of Insulin Absorption of Formulations BIOD 105 and BIOD 107 in Miniature Diabetic Swine The aim of this study was to evaluate the pharmacokinetic (PK) and pharmacodynamic (PD) properties of modified insulin formulations predicted to be associated with improved toleration. The addition of calcium EDTA to an insulin formulation (containing disodium EDTA) was shown in Example 1 to reduce the site reaction to the injection when compared to an insulin formulation containing disodium EDTA, without added calcium EDTA); however, the rapid action of the formulation was somewhat delayed from this substitution. Therefore, new insulin formulations were developed to regain the loss in timing (rapid action), and to improve stability. Additional citric acid was added (150% compared to the original formulation, VJ 7) to some formulations, and a ⅓ reduction in m-cresol was explored, to enhance stability.

In one of the new formulations, disodium EDTA and $CaCl_2$ were added as separate excipients to achieve the calcium chelated form of EDTA (BIOD 107). The rate of insulin absorption from BIOD 107 was compared to the rate of insulin absorption from an insulin formulation to which Ca EDTA (BIOD 105) was added directly, and to the rate of insulin absorption from VJ 7 (containing disodium EDTA, no added calcium).

Methods and Materials

Calcium-EDTA-citric acid formulation (BIOD 105) contains: 100 U/ml of insulin, 1.8 mg/ml of calcium disodium EDTA, 2.7 mg/ml of citric acid (=150% the amount in VJ 7), 20.08 mg/ml of glycerin, and 3.0 mg/ml of m-cresol.

$CaCl_2$-EDTA-citric acid formulation (BIOD 107) contains: 100 U/ml of insulin or an insulin analog, 1.8 mg/ml of disodium EDTA, 2.7 mg/ml of citric acid (=150% the amount in VJ 7), 18.1 mg/ml of glycerin, 2.0 mg/ml of m-cresol (=⅓ reduction in amount of m-cresol in VJ 7), and 5 mM of calcium chloride.

The formulations, VJ 7, BIOD 105 and 107, were subcutaneously injected into miniature swine, following which the rate of insulin absorption following subcutaneous administration of each test formulation was measured.

Six to eight diabetic miniature swine were injected in the morning with 0.25 U/kg of test formulation instead of their daily porcine insulin. Animals were fed 500 g of swine diet and plasma samples were collected at −30, −20, −10, 0, 5, 10, 15, 20, 30, 45, 60, 75, 90, 120, 150, 180, 240, 300 and 360 min post dose using a Becton Dickinson $K_2$EDTA vacutainer. Frozen plasmas were assayed for insulin content (#EZHI-14K Millipore, USA) and analyzed for glucose concentration (YSI 3200 analyzer, YSI Life sciences, USA).

Duration was estimated without non-linear modeling. The pharmacodynamic response was calculated from the time post dose required to drop the blood glucose level 20 points from baseline and the time for blood glucose to increase 20 points from nadir. The time between these parameters is defined as duration of action.

Absorption rate was calculated as the slope of line drawn from the initial increase in insulin concentration post injection (up to 30 min. post dose).

Results:

Absorption rate parameters are shown below in Table 4:

TABLE 4

Comparison of the initial rate of absorption of formulations BIOD 105 and BIOD 107 to the original formulation VJ7.

| | Abs. Rate (μU/mL/min) | Time to 20 pt drop (min.) |
|---|---|---|
| VJ 7 | 5.9 ± 1.6 | 7.4 ± 2.8 |
| BIOD-105 | 4.9 ± 2.2 | 8.5 ± 2.0 |
| BIOD-107 | 4.6 ± 1.5 | 5.5 ± 2.6 |

Time to 20 pt drop = time post dose to drop blood glucose concentration 20 points below baseline T-test comparisons showed that there is no statistical difference in the initial rate of absorption of these formulations. Although the shape of the curves in a plot of the concentration versus time profiles were slightly different, the initial rate of absorption curves were mostly superimposable. This ensures that the onset of insulin action is rapid.

Pharmacodynamic results are shown in Table 5 below.

TABLE 5

Pharmacodynamic parameter calculation.

| | VJ7 | BIOD 105 | BIOD 107 |
|---|---|---|---|
| Time to 20 pt drop (min.) | 7.0 ± 1.1 | 8.6 ± 0.8 | 5.5 ± .9 |
| Time to 20 pt recovery (min.) | 193.3 ± 47.0 | 222.4 ± 67.3 | 186.3 ± 39.3 |
| Duration (min) | 186.8 ± 47.2 | 213.7 ± 67.6 | 180.8 ± 38.7 |

Time to 20 pt drop = time post dose to drop blood glucose concentration 20 points below baseline
Time to 20 pt recovery = time post dose for blood glucose to increase 20 point post nadir
Duration is the time between time to 20 pt drop and time to 20 pt recovery.

The data shows pharmacokinetically and pharmacodynamically absorption profiles similar to the original formulation were achieved, despite substitution of disodium EDTA with calcium disodium EDTA and increasing in citrate ions.

Example 3

Insulin Formulations Containing Magnesium Salts

The effect of magnesium salts on the pharmacokinetics, pharmacodynamics and injection site discomfort obtained with insulin formulations containing disodium EDTA was assessed, compared to HUMLAOG®. Each milliliter of HUMLAOG® contains: insulin lispro 100 units, 16 mg glycerin, 1.88 mg dibasic sodium phosphate, 3.15 mg Metacresol, zinc oxide content adjusted to provide 0.0197 mg zinc ion, trace amounts of phenol, and water for Injection. Insulin lispro has a pH of 7.0 to 7.8. The pH is adjusted by addition of aqueous solutions of hydrochloric acid 10% and/or sodium hydroxide 10%.

Materials and Methods

Insulin formulations were prepared as described above in Table 1.

The formulations were evaluated in 12 human volunteers. The Demographic/Baseline information and Dose Summary are described in Table 6.

TABLE 6

Demographic/Baseline and Dose Summary

| Variable | Statistic/Category | |
|---|---|---|
| Sex | Female (%) | 2 (16.7%) |
| | Male (%) | 10 (83.3%) |
| Race | Black/African American | 1 (8.3%) |
| | White | 11 (91.7%) |
| Ethnicity | Hispanic/Latino | 2 (16.7%) |
| | Not Hispanic/Latino | 10 (83.3%) |
| Age (yrs) | Mean ± SD | 42.3 ± 8.9 |
| | Median | 43 |
| | Minimum, Maximum | 25, 58 |
| HbA1c (%) | Mean ± SD | 7.70 ± 0.79 |
| | Median | 7.8 |
| | Minimum, Maximum | 6.6, 8.8 |
| Dose(Units) | Mean ± SD | 16.3 ± 2.7 |
| | Median | 17 |
| | Minimum, Maximum | 11, 20 |

Results

The pharmacokinetics (Mean±SE) for BIOD 123, BIOD 125, and HUMLAOG® are shown in Table 7.

With respect to EDTA and Magnesium, BIOD-123 (shown in Table 1) contains disodium EDTA and $MgSO_4$, while BIOD-125 contains disodium EDTA (1.98 mg/ml); citric acid (2.7 mg/ml); glycerin (18 mg/ml); m-cresol (3 mg/ml); $CaCl_2$ (3.38 mg/ml); tween (1.53 mg/ml) and no magnesium compounds.

TABLE 7

Pharmacokinetics (Mean ± SE)

| Variable | BIOD-123 (n = 11) | BIOD-125 (n = 12) | HUMLAOG ® (n = 12) |
|---|---|---|---|
| Tins50% (Early) | 9.8 ± 1.1 | 12.4 ± 2.0 | 27.0 ± 2.7 |
| TinsMax | 46.4 ± 14.9 | 60.8 ± 15.2 | 65.0 ± 7.0 |
| Tins50% (Late) | 206.2 ± 34.5 | 179.2 ± 40.5 | 151.2 ± 11.0 |
| Cmax | 92.7 ± 17.3 | 75.9 ± 14.3 | 75.0 ± 8.8 |
| AUCins0-30 | 1803 ± 372 | 1331 ± 320 | 532 ± 107 |
| AUCins0-45 | 2926 ± 563 | 2182 ± 472 | 1404 ± 216 |
| AUCins0-60 | 3901 ± 710 | 2993 ± 611 | 2369 ± 314 |
| AUCins0-120 | 7166 ± 950 | 5966 ± 987 | 5663 ± 644 |
| AUCins0-480 | 14705 ± 699 | 13220 ± 1493 | 9080 ± 952 |
| AUCins120-480 | 7539 ± 887 | 7254 ± 1111 | 3417 ± 536 |

With respect to Tables 7 and 9, AUCins0-30=the 0-30 min area under the curve for insulin; AUCins0-45=the 0-45 min area under the curve for insulin; AUCins0-60=the 0-60 min area under the curve for insulin; AUCins0-120=the 0-120 min area under the curve for insulin; AUCins0-480=the 0-480 min area under the curve for insulin; AUCins120-480=the 120-480 min area under the curve for insulin.

The time related pharmacokinetic (PK) parameters (medians) are shown in Table 8.

TABLE 8

Time-Related PK Parameters (Medians)

| Variable | BIOD-123 | BIOD-125 | HUMLAOG ® |
|---|---|---|---|
| Tins50% (Early) | 9.6 | 9.4 | 25.9 |
| TinsMax | 25.0 | 30.0 | 67.5 |
| Tins50% Late | 169.7 | 140.0 | 149.8 |

The pharmacodynamics (LS means) are show in Table 9.

TABLE 9

Pharmacokinetics (LS means)

| Variable | BIOD-123 | BIOD-125 | HUMLAOG ® | P-value BIOD-123 vs HUMLAOG ® | P-value BIOD-125 vs HUMLAOG ® |
|---|---|---|---|---|---|
| Tins50% Early | 10.0 | 12.4 | 27.0 | <0.001 | <0.001 |
| TinsMax | 48.0 | 60.8 | 65.0 | 0.256 | 0.769 |
| Tins50% Late | 210.5 | 179.2 | 151.2 | 0.117 | 0.431 |
| Cmax | 89.5 | 75.9 | 75.0 | (0.264) | (0.942) |
| AUCins0-30 | 1779.8 | 1331.0 | 532.3 | (0.012) | (0.225) |
| AUCins0-45 | 2872.7 | 2181.5 | 1403.5 | (0.002) | (0.056) |
| AUCins0-60 | 3816.6 | 2993.0 | 2369.4 | (0.009) | (0.210) |
| AUCins0-120 | 6942.0 | 5965.7 | 5663.0 | (0.191) | (0.020) |
| AUCins0-480 | 14519 | 13220 | 9080 | (<0.001) | (0.005) |
| AUCins120-480 | 7493.2 | 7254.1 | 3417.0 | (<0.001) | (<0.001) |

P-values in parentheses were not planned and may not be valid because of differences between insulin and lispro assays. AUCins0-45 was unplanned.

TABLE 10

Pharmacodynamics(LS means)

| Variable | BIOD-123 | BIOD-125 | HUMLAOG ® | P-value BIOD-123 vs HUMLAOG ® | P-value BIOD-125 vs HUMLAOG ® |
|---|---|---|---|---|---|
| GIRmax (mg/kg/min) | 7.00 | 6.49 | 7.28 | 0.752 | 0.358 |
| TGIRmax (min) | 132.6 | 201.1 | 134.3 | 0.961 | 0.049 |
| TGIRearly50% (min) | 32.9 | 34.2 | 43.2 | 0.119 | 0.148 |
| TGIRlate50% (min) | 289.1 | 283.5 | 260.7 | 0.281 | 0.385 |
| GIRAUC0-30 (mg/kg) | 37.0 | 40.1 | 32.8 | 0.818 | 0.680 |
| GIRAUC0-60 (mg/kg) | 196.0 | 177.4 | 153.5 | 0.305 | 0.547 |
| GIRAUC0-120 (mg/kg) | 493.5 | 423.1 | 504.4 | 0.904 | 0.357 |
| GIRAUC0-180 (mg/kg) | 802.1 | 717.0 | 859.7 | 0.681 | 0.298 |
| GIRAUC0-480 (mg/kg) | 1575.7 | 1469.1 | 1466.0 | 0.571 | 0.987 |
| GIRAUC180-480 (mg/kg) | 781.4 | 752.0 | 606.3 | 0.053 | 0.091 |

Figure 2:
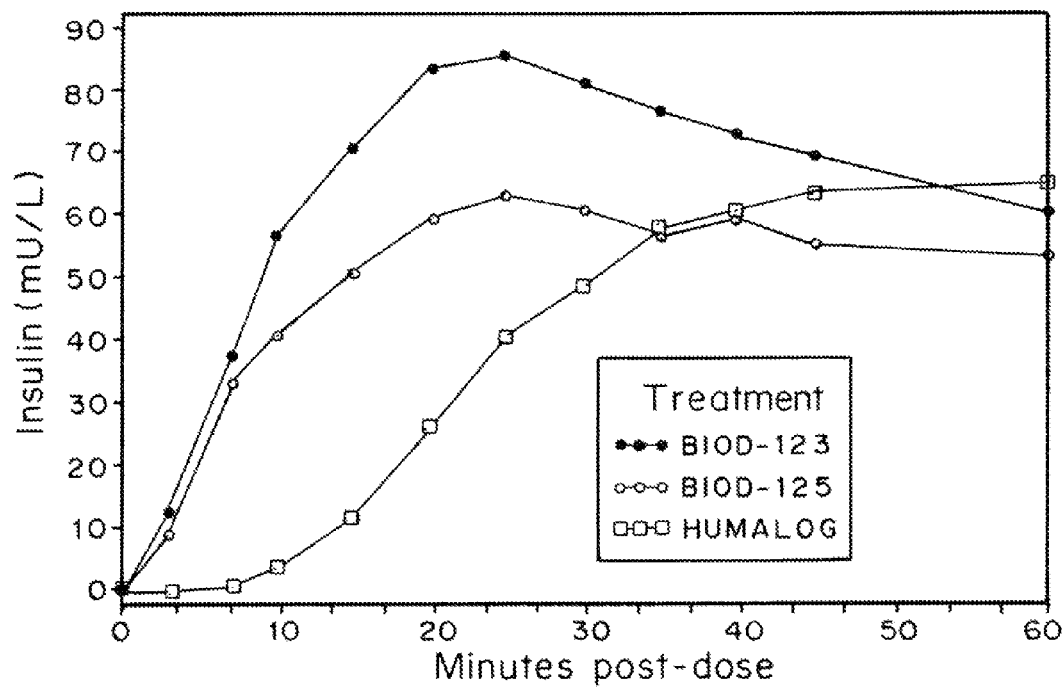
FIGS. 2 and 3 are graphs of mean insulin concentration (mU/L) as a function of time (FIG. 2, 0-60 minutes.
Figure 3:
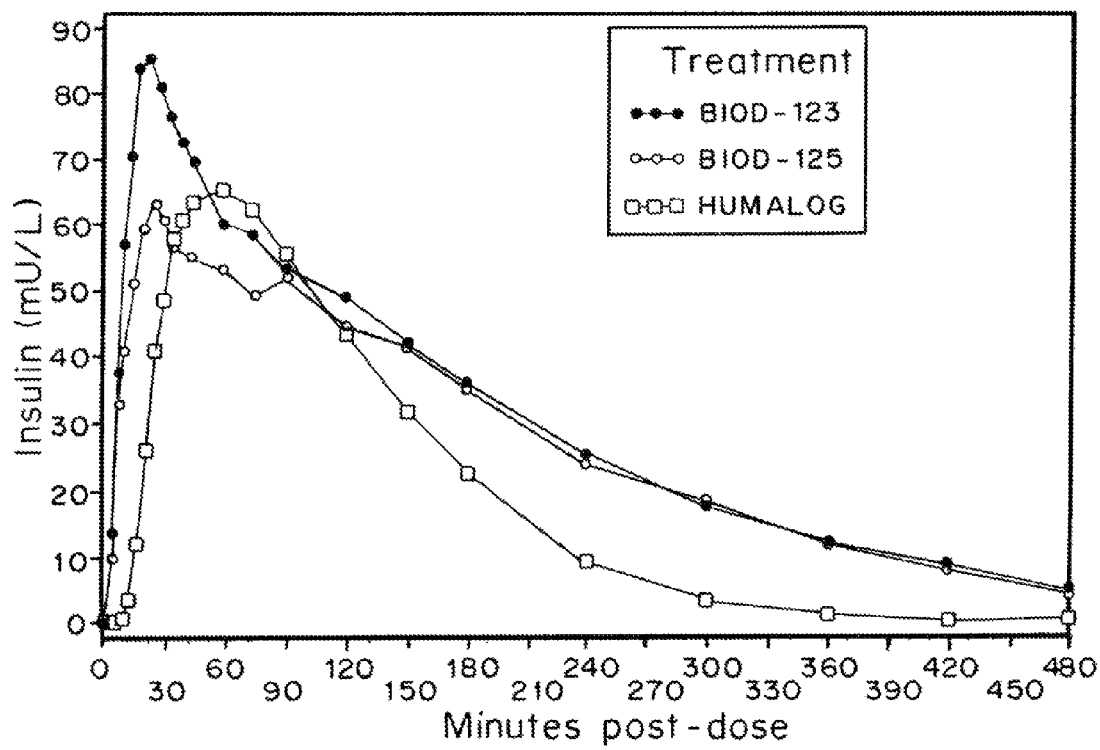
Figure 4:
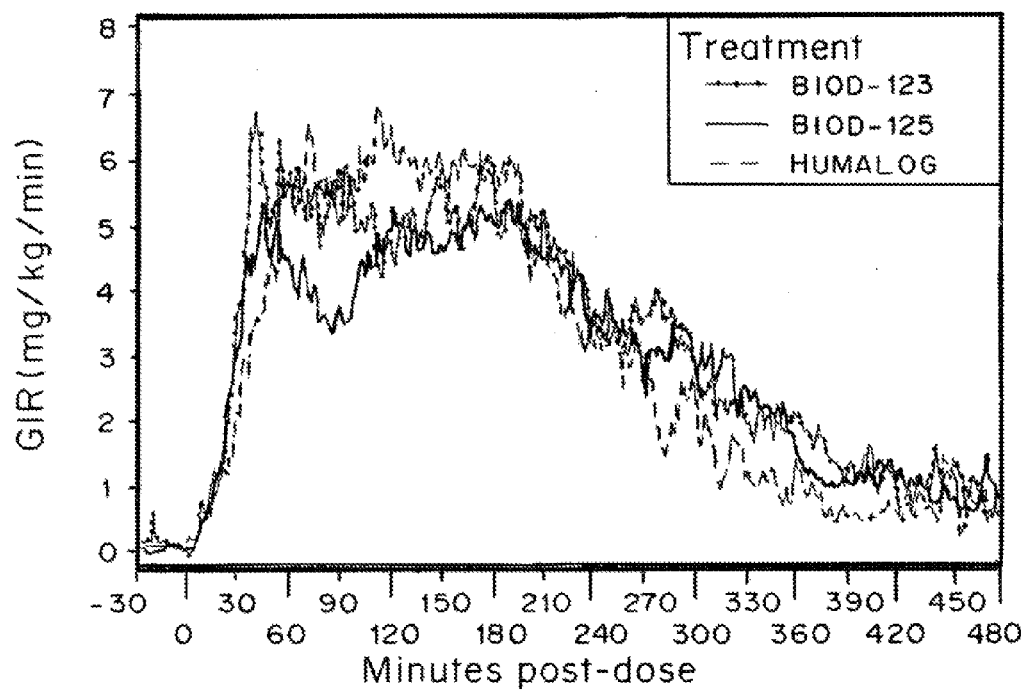
FIGS. 4 and 5 are graphs of mean GIR (mg/kg/min) as a function of time (minutes) of the Mg EDTA insulin formulations BIOD 123 and 125 compared to HUMALOG®.
Figure 5:
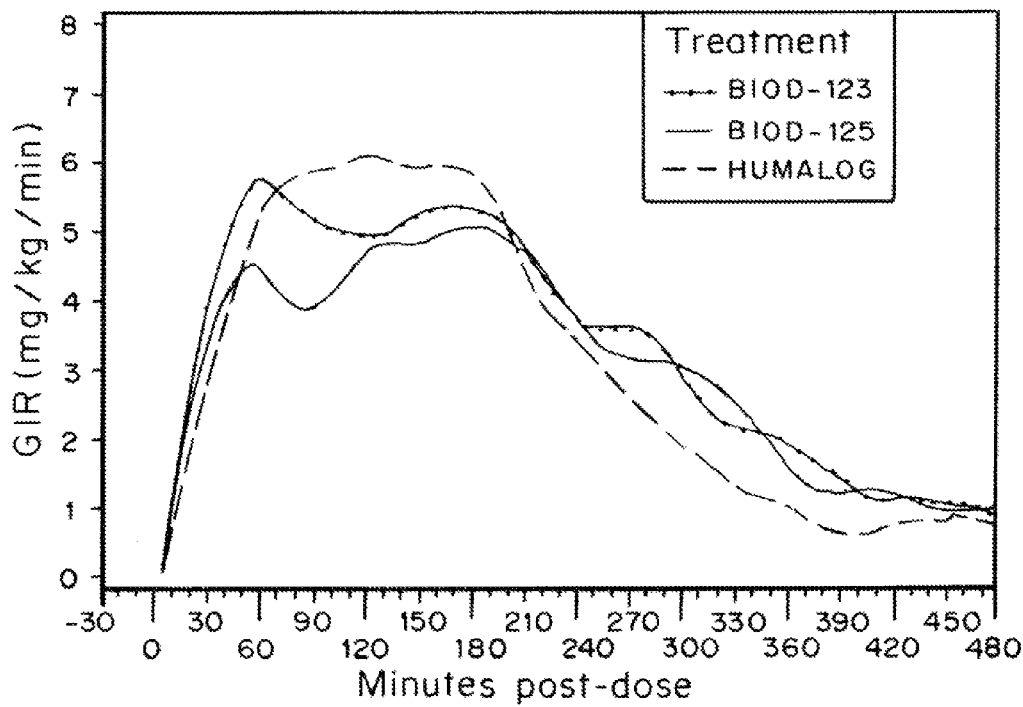

GIR is the glucose infusion rate (mg/kg/min), or amount of glucose required to clamp a subject within a normoglycemic range, typically 80-120 mg/dL following an insulin injection. The GIRmax is the maximal glucose infusion rate, which occurs at TGIRmax. The Half maximal rate occurs before the peak (GIRearly50%) and after the peak (GIRlate50%), at TGIR50% early and TGIR50% late. Areas under the GIR curve are estimated for the entire study duration GIRAUC0-480 (mg/kg) and segments of time between the beginning and end of the study, 0-30, 0-60, 0-120, 0-180, and 180-480 minutes. Graphic representation of the mean concentration vs. time profiles from time 0-60 min and 0-480 min are shown in FIGS. 2 and 3, respectively. FIGS. 4 and 5 are graphs of mean GIR (mg/kg/min) as a function of time (minutes) of the insulin formulations BIOD 123 and 125 compared to Humalog.

As shown in Tables 7-10 and FIGS. 2-5, BIOD-125 (which contains disodium EDTA, $CaCl_2$ and no magnesium compounds) showed more rapid in vivo absorption than BIOD-123 (which contains disodium EDTA and $MgSO_4$).

Information regarding injection site discomfort is shown in the following tables. Table 11 shows Injection Site Discomfort Results—Safety Population (LS means) and severity of injection site discomfort.

TABLE 11

Injection Site Discomfort Results - Safety Population (LS means) and Severity of Injection Site discomfort

| Variable | BIOD-123 | BIOD-125 | HUMLAOG ® | P-value BIOD-123 vs HUMLAOG ® | P-value BIOD-125 vs HUMLAOG ® |
|---|---|---|---|---|---|
| VAS | 2.9 | 6.8 | 2.1 | 0.600 | 0.023 |
| Severity Score (absolute) | 0.32 | 0.50 | 0.17 | 0.376 | 0.059 |
| Severity Score (relative) | 2.92 | 3.08 | 2.85 | 0.749 | 0.424 |
| Injection Site Discomfort Severity | | | | | |
| Treatment | | | | | |
| None | 7 (63.4%) | 7 (58.3%) | 10 (83.3%) | | |
| Mild | 4 (36.4%) | 4 (33.3%) | 2 (16.7%) | | |
| Moderate | 0 | 1 (8.3%) | 0 | | |
| Severe | 0 | 0 | 0 | | |

Note:
VAS 0 = No Discomfort, 100 = Worst Possible; Severity 0 = None, 1 = Mild, etc; Relative Discomfort 2 = Less than Usual, 3 = Equal to Usual, etc.
VAS Results (Arithmetic Mean ± SE); BIOD-123 = 3.6 ± 2.; BIOD-125 = 6.8 ± 2.9; Humalog = 1.8 ± 1.1

Table 12 shows the injection site discomfort relate to usual meal time insulin injection.

TABLE 12

Injection Site Discomfort Relative to Usual Meal Time Insulin Injection

| Treatment | Much Less | Less | Equal | Increased | Greatly Increased |
|---|---|---|---|---|---|
| BIOD-123 (n = 12) | 1 (9.1%) | 1 (9.1%) | 7 (63.4%) | 2 (18.2%) | 0 |
| BIOD-125 (n = 12) | 1 (8.3%) | 0 | 9 (75.0%) | 1 (8.3%) | 1 (8.3%) |
| HUMLAOG ® (n = 12) | 0 | 1 (8.3%) | 11 (91.7%) | 0 | 0 |

Information regarding the type of discomfort, the time of onset, and the duration are shown in Table 13.

TABLE 13

Injection Site Discomfort Description

| Treatment | Irritation (Burning) | Other | Pain (Stinging) |
|---|---|---|---|
| BIOD-123 | 2 | 0 | 2 |
| BIOD-125 | 1 | 2 | 2 |
| HUMLAOG ® | 1 | 0 | 1 |

Injection Site Discomfort Onset

| Treatment | <10 sec | 10 sec-1 min | 1-10 min |
|---|---|---|---|
| BIOD-123 | 3 | 0 | 1 |
| BIOD-125 | 1 | 4 | 0 |
| HUMLAOG ® | 1 | 1 | |

Injection Site Discomfort Duration

| Treatment | ≤30 sec | >30 sec-<5 min |
|---|---|---|
| BIOD-123 | 2 | 2 |
| BIOD-125 | 0 | 5 |
| HUMLAOG ® | 1 | 1 |

As shown above, the formulation containing a magnesium compound (BIOD-123, $MgSO_4$), showed significantly less injection site discomfort than the corresponding compound without $MgSO_4$ (BIOD-125). The duration of discomfort for BIOD-123 was significantly less than for BIOD-125 (Table 13).

Example 4

Human Study with BIOD-250 and BIOD-238 Demonstrating Reduced Injection Site Pain and Ultra-Rapid Action A Phase 1 clinical trial of two ultra-rapid-acting insulin analog-based formulations, BIOD-238 and BIOD-250, evaluated the pharmacokinetic and injection site toleration profiles relative to HUMALOG® (insulin lispro), a rapid-acting insulin analog. BIOD-238 and BIOD-250 are combinations of Biodel's proprietary excipients with the marketed formulation of HUMALOG®. The composition of BIOD-250 is shown in Table 1. BIOD-238 has similar composition except it does not have magnesium, and has less EDTA (0.225 mg/ml).

The single-center, randomized, double-blind, three-period crossover trial in 12 patients with Type 1 diabetes was conducted in Australia. Each study drug was administered subcutaneously on separate days. Pharmacokinetic measurements were made using an assay to quantify the active ingredients in the study drugs and HUMALOG®. The clinical trial was powered to measure differences in time to half-maximal insulin concentrations. The hypothesis tested in this study was than Biodel's formulations of HUMALOG® would have ultra-rapid absorption profiles with comparable declines from peak concentration and comparable injection site tolerability profiles relative to HUMALOG®. Two approaches were taken to mitigate injection site discomfort—reducing disodium EDTA concentrations (BIOD-238) and addition of magnesium sulfate (BIOD-250), which was observed to improve toleration in a previous study.

The pharmacokinetic profiles of BIOD-238 and BIOD-250 proved to be consistent with the target product profile for analog-based ultra-rapid-acting insulin. Absorption rates of BIOD-238 and BIOD-250 were significantly more rapid than that of HUMALOG®, as indicated by 35-45% reductions in mean times to half maximal insulin concentrations ($p<0.001$ for BIOD-238 and $p=0.001$ for BIOD-250 vs. HUMALOG®) and time to maximal insulin concentrations ($p=0.013$ for BIOD-238 and $p=0.025$ for BIOD-250 vs. HUMALOG®). Furthermore, the total amount of insulin absorbed over the first 30 minutes following injection of BIOD-238 and BIOD-250 was approximately double that seen for HUMALOG® ($p<0.001$ for BIOD-238 and $p=0.002$ for BIOD-250 vs. HUMALOG®). The decline from peak concentration, as indicated by time to half maximal concentration after the peak, was significantly shorter for both BIOD-238 and BIOD-250 compared to HUMALOG® ($p=0.009$ for BIOD-238 and $p=0.016$ for BIOD-250 vs. HUMALOG®).

Local injection site discomfort was measured with a 100 mm visual analog scale (VAS) and patient questionnaires. 100 mm is defined as the worst possible discomfort and 0 mm is defined a having no discomfort. In the trial, the VAS score was numerically lower, but not significantly different for BIOD-250 compared to HUMALOG® (mean VAS scores of 2.7 mm and 8.2 mm for BIOD-250 and HUMALOG®, respectively; p=NS). The VAS score for BIOD-238 was significantly higher than that associated with HUMALOG® (mean VAS score of 24.2 mm, $p=0.029$ vs. HUMALOG®). The pharmacokinetic profiles of BIOD-238, BIOD-250 and HUMALOG® as well as their Injection Site Toleration Profiles are shown in Tables 14 and 15, respectively

TABLE 14

Pharmacokinetic Profiles of BIOD-238, BIOD-250 and HUMALOG ®

| | Variable | BIOD-238 N = 10 | BIOD-250 N = 11 | HUMALOG ® N = 10 | P-value BIOD-238 vs. HUMALOG ® | P-value BIOD-250 vs. HUMALOG ® |
|---|---|---|---|---|---|---|
| Absorption | Early ½ $T_{max}$ (minutes) | 13.7 ± 1.9 (13.6) | 14.6 ± 1.9 (12.9) | 24.8 ± 2.9 (22.6) | <0.001 | 0.001 |
| | $T_{max}$ (minutes) | 35.5 ± 2.5 (37.5) | 40.9 ± 6.1 (40.0) | 62.5 ± 8.4 (60.0) | 0.013 | 0.025 |
| | $AUC_{ins0-30}$ (mU*min/L) | 1278 ± 164 (1105) | 1186 ± 133 (1260) | 598 ± 126 (654) | <0.001 | 0.002 |
| | $AUC_{ins0-45}$ (mU*min/L) | 2421 ± 245 (2132) | 2160 ± 195 (2327) | 1486 ± 216 (1458) | <0.001 | 0.010 |
| | $AUC_{ins0-60}$ (mU*min/L) | 3476 ± 326 (3197) | 3081 ± 245 (3125) | 2505 ± 280 (2358) | 0.002 | 0.066 |
| Decline from peak concentration | Late ½ $T_{max}$ (minutes) | 123.8 ± 10.5 (125.3) | 132.3 ± 18.7 (117.0) | 166.5 ± 10.6 (183.4) | 0.009 | 0.016 |

Data represent the Mean ± SEM; Median Values are presented in parentheses.

TABLE 15

Injection Site Toleration Profiles of
BIOD-238, BIOD-250 and HUMALOG ®
Injection Site Toleration Profiles of
BIOD-238, BIOD-250 and HUMALOG ®

| Metrics | BIOD-238 N = 10 | BIOD-250 N = 11 | HUMALOG ® N = 10 |
|---|---|---|---|
| Tolerability (VAS 0-100 mm) | 24.2 ± 7.0* (15.0) | 2.7 ± 1.6 (0.0) | 8.2 ± 4.5 (2.0) |
| Absolute Severity Score | 1.09 ± 0.2* (1.0) | 0.1 ± 0.1 (0.0) | 0.5 ± 0.2 (0.0) |
| Relative Severity Score | 3.6 ± 0.03 (4.0) | 2.9 ± 0.02 (3.0) | 3.2 ± 0.1 (3.0) |

Data represent the Mean ± SEM; Median Values are presented in parentheses.
100 mm Visual Analog Scale (VAS): 0 = no discomfort, 100 = worst possible discomfort
Absolute Severity Scale: 0 = None, 1 = Mild, 2 = Moderate, 3 = Severe
Relative Severity (compared to usual meal-time insulin injections): 1 = Much less, 2 = Less, 3 = Equal, 4 = Increased, 5 = Greatly increased;
*p < 0.05 vs. HUMALOG ®

In conclusion, this study demonstrates that EDTA and citrate formulations of insulin lispro (both BIOD-238 and BIOD-250) have more rapid absorption rates and more rapid declines from peak concentrations compared to HUMALOG®. Furthermore, the presence of magnesium sulfate in BIOD-250 significantly mitigates local injection site discomfort without altering the ultra-rapid pharmacokinetic profile of BIOD-238.

Example 5

The PK and PD of Rapid Acting Concentrated Insulin Formulation Compared to Commercial U-500 Formulation in Diabetic Miniature Swine The aim of the present study was to evaluate the pharmacokinetic (PK) and pharmacodynamic (PD) properties of a new U-400 concentrated insulin formulation designed for prandial use.

Methods and Materials

The composition of the formulation BIOD-530 was: 3.6 mg/ml EDTA, 1.8 mg/ml trisodium citrate, 2 mg/ml m-cresol, 16 mg/ml glycerin, 12.12 mg/ml insulin (400 U/mL).

Up to 10 diabetic miniature swine were injected in the morning with 0.25 U/kg of Lilly U-500R or BIOD-530, instead of their daily insulin. Animals were fed 500 g of swine diet directly after dosing and plasma samples were collected at −30, −20, −10, 0, 5, 10, 15, 20, 30, 45, 60, 75, 90, 120, 150, 180, 240, 300, 360, 420 and 480 min post dose using a Becton Dickinson $K_2$EDTA vacutainer. Frozen plasmas were assayed for insulin content (isoinsulin kit, Mercodia, USA) and analyzed for glucose concentration (YSI 3200 analyzer, YSI Life sciences, USA).

Figure 6:
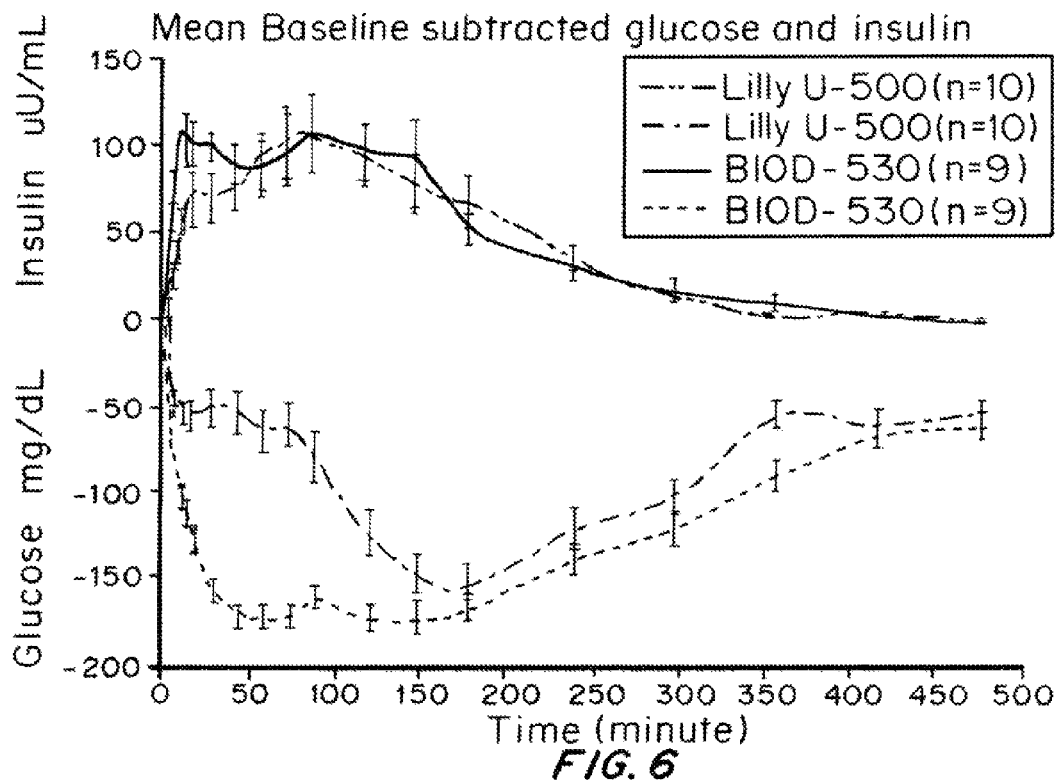
FIG. 6 shows the mean baseline subtracted insulin (solid lines) and glucose (dotted lines) vs. time in diabetic miniature swine. BIOD-530 (black) and Lilly U-500 (grey), ±SEM.

Results:

The pharmacokinetic profile is shown graphically in FIG. 6, and calculated PK parameters are in Table 17.

TABLE 17

Calculated PK parameters:

| | Lilly U-500 | BIOD-530 |
|---|---|---|
| Cmax | 135.5 ± 22.7 | 159.5 ± 18.7 |
| Tmax | 94 ± 17.1 | 41.7 ± 12.2* |
| $T_{1/2\ max}$ | 26.9 ± 5.0 | 11.1 ± 2.1* |

*p < 0.05

The pharmacodynamics are shown graphically as the mean of baseline subtracted glucose over time in FIG. 6.

Conclusion

The data shows the concentrated insulin formulation has a rapid action profile compared to the Lilly U-500 commercial formulation. The rapidity of the BIOD-530 formulation may be sufficient for prandial use.

Example 6

Comparison of HUMALOG® (U-100) to BIOD-530 and BIOD-531 in Diabetic Miniature Swine The aim of the present study was to evaluate the pharmacokinetic (PK) and pharmacodynamic (PD) properties of a U-400 concentrated insulin formulation with Magnesium (BIOD-531) (TABLE 1) and a formulation without Magnesium (BIOD-530) (see Example 4) compared to HUMALOG®, a rapid acting U-100 analog insulin for prandial use.

Methods and Materials

The composition of the formulation BIOD-530 was: 3.6 mg/ml EDTA, 1.8 mg/ml trisodium citrate, 2 mg/ml m-cresol, 16 mg/ml glycerin, 12.12 mg/ml insulin (400 U/mL). BIOD-531 was the same composition as BIOD-530 with 4 mm Mg $SO_4$ added, intended to improve injection site tolerability.

Using a crossover study design, 9 diabetic miniature swine were injected in the morning with 0.25 U/kg of BIOD-530, BIOD-531 or HUMALOG® instead of their daily insulin. Animals were fed 500 g of swine diet directly after dosing and plasma samples were collected at −30, −20, −10, 0, 5, 10, 15, 20, 30, 45, 60, 75, 90, 120, 150, 180, 240, 300, 360, 420 and 480 min post dose using a Becton Dickinson $K_2$EDTA vacutainer. Frozen plasmas were assayed for insulin content (iso insulin kit, Mercodia) and analyzed for glucose concentration (YSI 3200 analyzer, YSI Life sciences, USA).

Figure 7:
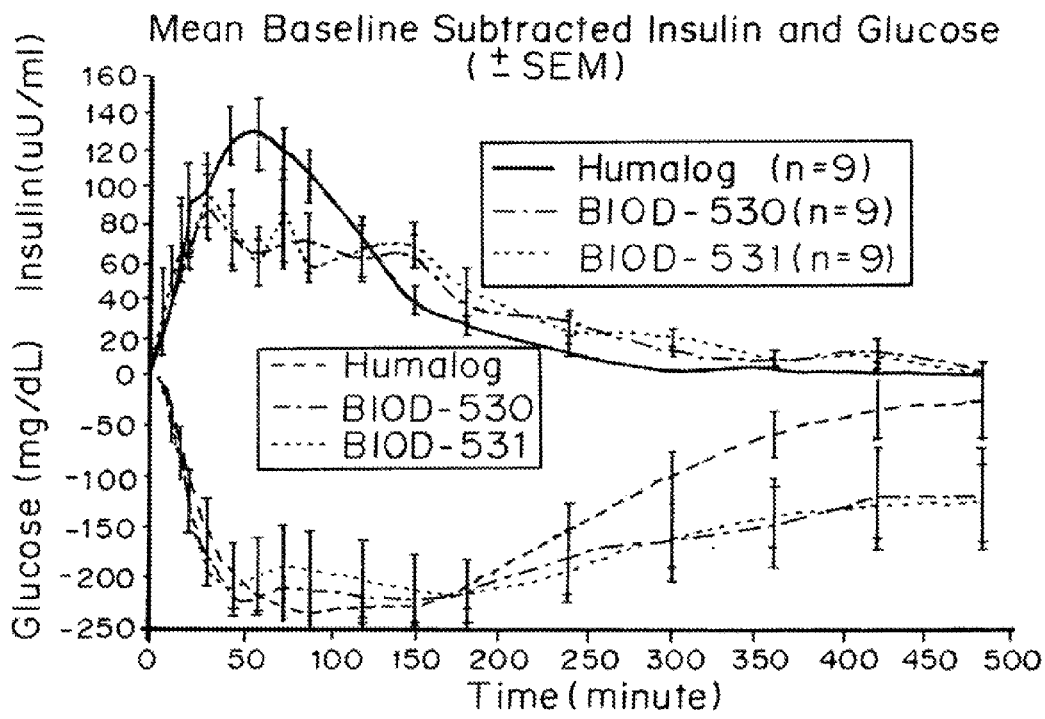
FIG. 7 is a graph of the mean baseline subtracted insulin (solid lines) and glucose lowering (dashed lines) of BIOD-530 (dark grey), BIOD-531 (light grey) and HUMALOG® (black) in diabetic swine. n=9, ±SEM.

Results:

Mean baseline subtracted insulin and glucose concentration vs. time is shown in FIG. 7. The pharmacokinetic parameters are in Table 18. The time to maximal concentration Tmax was similar across the formulations, while the time to half maximal concentration (½Tmax) trended earlier with the BIOD formulations.

TABLE 18

Pharmacokinetic Profiles of BIOD-530, BIOD-531 and HUMLOG ®

| Study 0.023 | HUMALOG ® | BIOD-530 | BIOD-531 |
|---|---|---|---|
| $C_{max}$ | 153 ± 14 | 108 ± 15 | 125 ± 16 |
| $T_{max}$ | 55 ± 7.5 | 67 ± 15 | 76 ± 16 |
| ½Tmax | 21 ± 4 | 9.6 ± 1.4 | 11 ± 9 |
| AUC | 16656 ± 1440 | 16508 ± 2482 | 17724 ± 2293 |

Conclusion: The addition of Magnesium to the formulation did not alter the pharmacokinetic or pharmacodynamic profile of BIOD-530. In addition, both the concentrated formulation, BIOD-530 and 531 were at least as rapid absorbing as HUMALOG®, and had a slightly faster onset of action than HUMALOG®. The total duration of action the U-400 formulations was longer THAN HUMALOG®.

Example 7

Reduction of Disodium EDTA and Loss of Rapid Absorption in Diabetic Miniature Swine The purpose of this study was to find the lowest EDTA concentration that was effective in maintaining an ultra-rapid absorption pharmacokinetic profile. Two formulations were made with successively less EDTA concentration than BIOD-530.

BIOD-532 had 2.7 mg/ml disodium EDTA and BIOD-533 had 1.8 mg/ml disodium EDTA. The rest of the components remained the same composition as BIOD-530 (See Example 4).

Using a crossover study design, 9 diabetic miniature swine were injected in the morning with 0.25 U/kg of BIOD-530, BIOD-532 or BIOD-533 instead of their daily insulin. Animals were fed 500 g of swine diet directly after dosing and plasma samples were collected at −30, −20, −10, 0, 5, 10, 15, 20, 30, 45, 60, 75, 90, 120, 150, 180, 240, 300, 360, 420 and 480 min post dose using a Becton Dickinson $K_2$EDTA vacutainer. Frozen plasmas were assayed for insulin content (iso insulin kit, Mercodia) and analyzed for glucose concentration (YSI 3200 analyzer, YSI Life sciences, USA).

Figure 8:
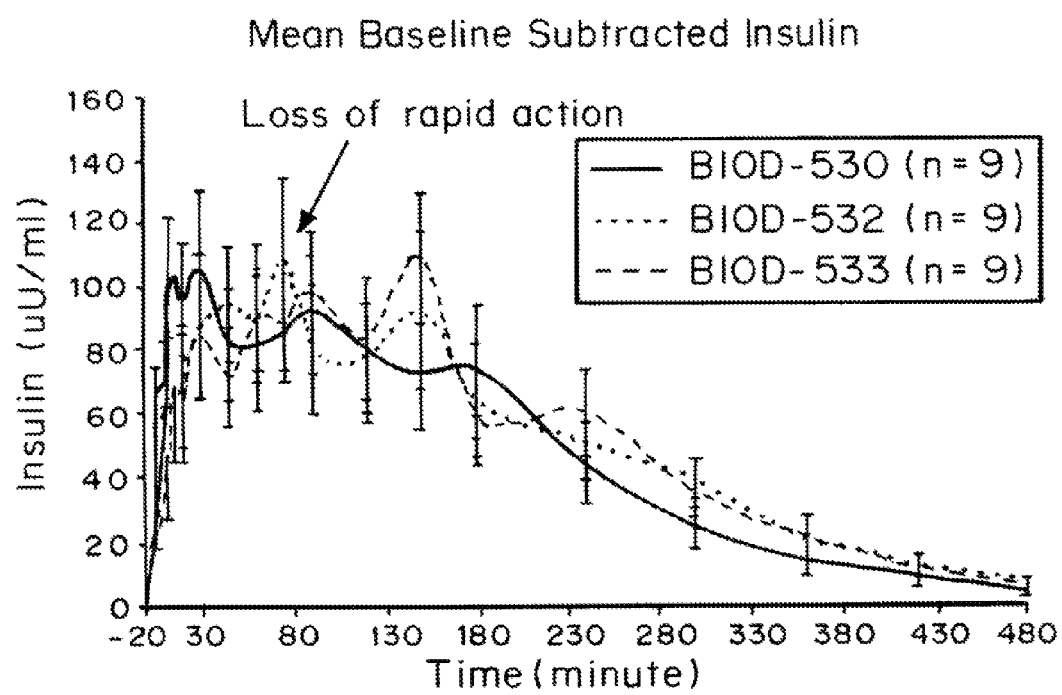
FIG. 8 shows the mean baseline subtracted insulin concentration vs. time of BIOD-530 (black), BIOD-532 (dark grey) and BIOD-533 (light grey) in miniature diabetic swine. n=9, ±SEM.

Results:

The concentration vs. time profile is shown in FIG. 8 and pharmacokinetic parameters in Table 19. Though the AUC and Cmax were consistent across the formulations, the early onset of absorption was lost as less EDTA was added.

TABLE 19

Pharmacokinetic Profiles of BIOD-530, BIOD-532 and BIOD 533

|  | BIOD-530 | BIOD-532 | BIOD-533 |
|---|---|---|---|
| $C_{max}$ | 137.7 ± 17.8 | 139 ± 21 | 145 ± 21 |
| $T_{max}$ | 36.1 ± 9.3 | 58.9 ± 11.8 | 103 ± 28 |
| ½Tmax | 10.3 ± 2.8 | 21.5 ± 4.6* | 29 ± 7* |
| AUC | 22674 ± 4585 | 24102 ± 4573 | 24427 ± 3830 |

Conclusion: In order to maintain the rapid onset of insulin absorption, greater than 2.7 mg/mL of disodium EDTA must be used.

Example 8

Comparison of BIOD-531 to HUMALOG® 75/25 in Diabetic Miniature Swine

The purpose of this study was to compare the pharmacokinetic profile of BIOD-531, U-400 (regular human insulin with magnesium), with the commercially available HUMALOG® 75/25 mix.

Using a crossover study design, 9 diabetic miniature swine were injected in the morning with 0.25 U/kg of BIOD-531, or HUMALOG® 75/25 mix instead of their daily insulin. Animals were fed 500 g of swine diet directly after dosing and plasma samples were collected at −30, −20, −10, 0, 5, 10, 15, 20, 30, 45, 60, 75, 90, 120, 150, 180, 240, 300, 360, 420 and 480 min post dose using a Becton Dickinson $K_2$EDTA vacutainer. Frozen plasmas were assayed for insulin content (iso insulin kit, Mercodia) and analyzed for glucose concentration (YSI 3200 analyzer, YSI Life sciences, USA).

Figure 9:
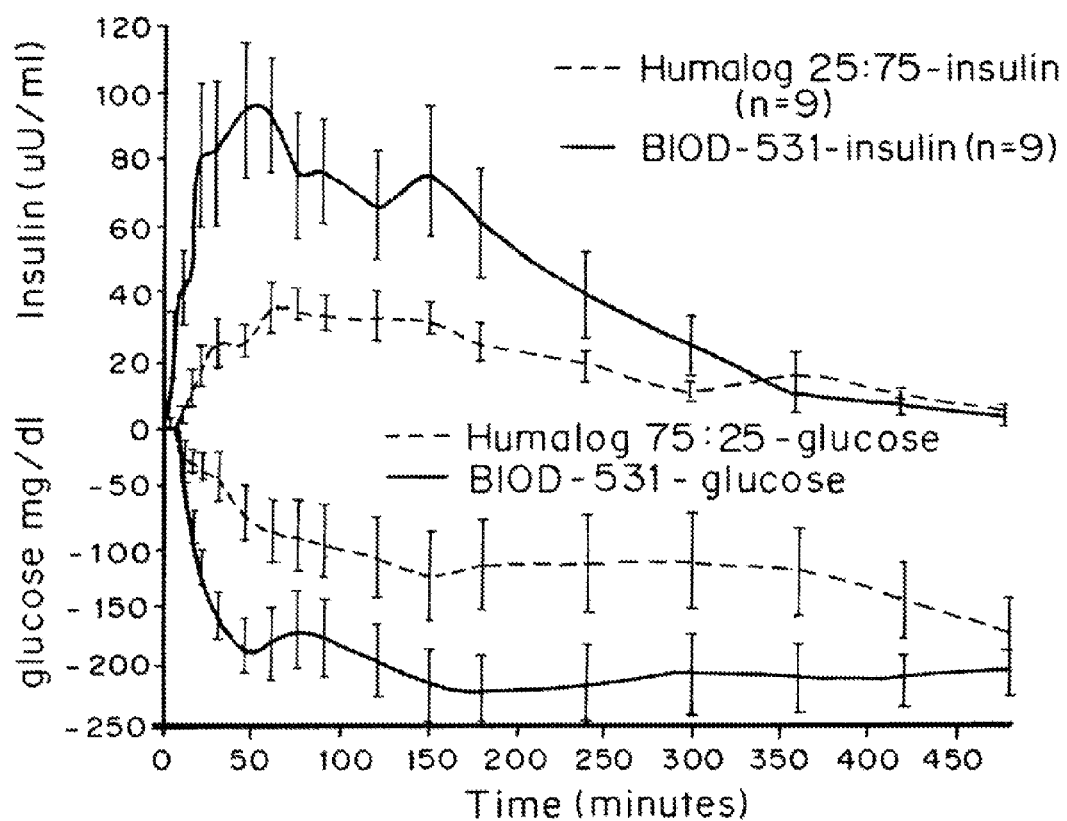
FIG. 9 shows the mean baseline subtracted insulin (solid lines) and glucose (dotted lines) vs. time in diabetic miniature swine. BIOD-531 (black) and HUMALOG® 75/25 (grey), ±SEM.

Results: The mean baseline subtracted insulin and glucose concentration vs. time is shown in FIG. 9 and the pharmacokinetic parameters are estimated in Table 18. BIOD-531 showed a considerable higher Cmax concentration and AUC. Though the half maximal timing is faster than the HUMALOG® mix, it is clear that the rate of absorption of the BIOD-531 is considerably faster (FIG. 9). Also, BIOD-531 has a glucose response is faster to nadir than The HUMALOG® mix, and remains there for the duration of the study.

TABLE 20

Pharmacokinetic Profiles of HUMLOG ® and BIOD 531

|  | HUMLOG ® 75/25mix | BIOD-531 |  |
|---|---|---|---|
| Cmax | 55 ± 5 | 131 ± 21* | p = .009 |
| Tmax | 86 ± 19 | 79 ± 18 | p = .79 |
| ½Tmax | 35 ± 6 | 24.6 ± 5 | p = .29 |
| AUC | 9673 ± 1167 | 20188 ± 4192* | p = .02 |

Conclusions: HUMALOG® 75/25 mix is a formulation intended to have a prandial and basal pharmacokinetic profile. BIOD-531 is more rapidly absorbed and has a sustained insulin action, making it suitable for prandial and basal use.

We claim:

1. An injectable insulin consisting of insulin monomers forming a hexamer in the presence of zinc, and a pharmaceutically acceptable excipient comprising zinc, an effective amount of a zinc chelator selected from the group consisting of ethylenediaminetetraacetic acid (EDTA), EGTA, alginic acid, alpha lipoic acid, dimercaptosuccinic acid (DMSA), CDTA (1,2-diaminocyclohexanetetraacetic acid), and trisodium citrate (TSC) to chelate the zinc to keep the insulin monomers and dimers dissociated; and an effective amount of a dissolution/stabilizing diacid or polyacid which stabilizes the dissociated insulin monomers and dimers; the improvement comprising
an effective amount of one or more magnesium salts from about 0.1 to about 10 mg/nil to decrease injection site discomfort as compared to the injection site discomfort with the formulation in the absence of the one or more magnesium compounds.

2. The formulation of claim 1 wherein the insulin is human recombinant insulin.

3. The formulation claim 1 where the insulin is an insulin analog.

4. The formulation of claim 1 wherein the insulin concentration is 100, 200, 400 or 500 U/mL.

5. The formulation of claim 1, wherein the one or more magnesium salts are selected from the group consisting of inorganic magnesium salts, organic magnesium salts, and combinations thereof.

6. The formulation of claim 5, wherein the inorganic magnesium salts are selected from the group consisting of magnesium hydroxide ($Mg(OH)_2$), magnesium sulfate ($Mg(SO_4)_2$), magnesium halides, magnesium chloride ($MgCl_2$), magnesium bromide ($MgBr_2$), magnesium iodide ($MgI_2$); magnesium pyrophosphate, magnesium sulfate heptahydrate, magnesium oxide ($MgO_2$), and combinations thereof.

7. The formulation of claim 5, wherein the organic magnesium salts are selected from the group consisting of magnesium EDTA, magnesium lactate, magnesium aspartate; magnesium acetate, magnesium carbonate ($Mg(CO_3)_2$), magnesium citrate, and magnesium gluconate.

8. The formulation of claim 1, wherein the one or more magnesium salts are $Mg(OH)_2$, $MgSO_4$, magnesium EDTA, or combinations thereof.

9. The formulation of claim 1, wherein the concentration of the one or magnesium salts from about 0.1 to about 5 mg/ml, from about 0.1 to about 2 mg/ml, or from about 0.2 to about 2 mg/ml.

10. The formulation of claim 1, wherein the formulation contains about 0.2-0.3 mg/ml $Mg(OH)_2$, about 1.7-2.0 magnesium EDTA, about 0.4-0.5 magnesium sulfate, or combinations thereof.

11. The formulation of claim 1 wherein the dissolution/stabilization agent is selected from the group consisting of acetic acid, ascorbic acid, citric acid, glutamic, succinic, aspartic, maleic, fumaric, adipic acid, and salts thereof.

12. The formulation of claim 1 wherein the dissolution/stabilization agent forms citric ions and the pH is about 7.

13. The formulation of claim 11 wherein the dissolution/stabilization agent is citric acid or sodium citrate.

14. The formulation of claim 11 wherein the dissolution/stabilization agent is citric acid or sodium citrate in a range of $2.0 \times 10^{-4}$ M to $4.5 \times 10^{-3}$ M.

15. The formulation of claim 1 wherein the dissolution/stabilization agent is citric acid or sodium citrate in a range between $7 \times 10^{-3}$ M and $2 \times 10^{-2}$ M.

16. The formulation of claim 1 wherein the dissolution/stabilization agent is citric acid or sodium citrate at about $9.37 \times 10^{-3}$ M or about $1.4 \times 10^{-2}$ M.

17. The formulation of claim 1 further comprising calcium chloride.

18. The formulation of claim 1 further comprising glycerine and m-cresol.

19. The formulation of claim 1, wherein the chelator is sodium EDTA.

20. An insulin formulation comprising 100 U/ml of human recombinant insulin, about 1.5 mg/ml anhydrous citric acid, about 1.5 mg/ml sodium EDTA, about 18 mg/ml of glycerin, about 0.481 mg/ml $MgSO_4$, and about 3.0 mg/ml of m-cresol at a pH of about 7.0.

21. An insulin formulation comprising 400 U/mL of human recombinant insulin 3.6 mg/ml EDTA, 1.8 mg/ml trisodium citrate, 2 mg/ml m-cresol, 16 mg/ml glycerin, 12.12 mg/ml insulin (400 U/mL) and 0.481 mg/ml $MgSO_4$.

22. A method of treating a diabetic individual comprising injecting into the individual an effective amount of the formulation of claim 1.

23. A method of decreasing injection site pain of insulin into a diabetic individual comprising injecting the individual with an effective amount of the formulation of claim 1.

24. The formulation of claim 1 wherein the zinc chelator is disodium EDTA, calcium disodium EDTA, or a combination thereof.

25. The formulation of claim 6, wherein the inorganic magnesium salt is magnesium sulfate ($Mg(SO_4)_2$).

* * * * *